(12) United States Patent
Tachikawa et al.

(10) Patent No.: US 10,604,758 B2
(45) Date of Patent: *Mar. 31, 2020

(54) THERAPEUTIC OLIGOMERS FOR TREATING AMYLOIDOSIS

(71) Applicant: Arcturus Therapeutics, Inc., San Diego, CA (US)

(72) Inventors: Kiyoshi Tachikawa, San Diego, CA (US); Joseph E. Payne, San Diego, CA (US); Padmanabh Chivukula, San Diego, CA (US)

(73) Assignee: ARCTURUS THERAPEUTICS, INC., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/859,571

(22) Filed: Dec. 31, 2017

(65) Prior Publication Data

US 2018/0135051 A1    May 17, 2018

Related U.S. Application Data

(63) Continuation of application No. 14/807,223, filed on Jul. 23, 2015, now Pat. No. 9,856,475, which is a
(Continued)

(51) Int. Cl.
*C12N 15/113*    (2010.01)
*A61K 9/127*    (2006.01)
(Continued)

(52) U.S. Cl.
CPC ............ *C12N 15/113* (2013.01); *A61K 9/127* (2013.01); *A61K 31/685* (2013.01);
(Continued)

(58) Field of Classification Search
None
See application file for complete search history.

(56) References Cited

U.S. PATENT DOCUMENTS 4,199,574 A    4/1980  Schaeffer
4,968,686 A   11/1990  Townsend
(Continued)

FOREIGN PATENT DOCUMENTS

WO    WO-96029336 A1    9/1996
WO    WO-99008688 A1    2/1999
(Continued)

OTHER PUBLICATIONS

Bartlett, "Effect of siRNA Nuclease Stability on the In Vitro and In Vivo Kinetics of siRNA-Mediated Gene Silencing," Biotechnology and Bioengineering, vol. 97, No. 4, Jul. 1, 2007.
(Continued)

*Primary Examiner* — J. E. Angell
(74) *Attorney, Agent, or Firm* — Mintz, Levin, Cohn, Ferris, Glovsky and Popeo, P.C.

(57) ABSTRACT

This invention provides pharmaceutical compositions containing a UNA oligomer targeted to TTR and a pharmaceutically acceptable carrier. The compositions can be used in methods for treating or preventing TTR-related amyloidosis in a primate. The compositions, upon administering a single dose to the primate, can reduce TTR protein in the primate for a period of days to weeks.

18 Claims, 11 Drawing Sheets

Specification includes a Sequence Listing.

```
                                          284
V30M TTR mRNA                             .         SEQ ID NOS: 103-118

3'- 304-UCGGAAAGACUUGUGUACGUACCGGUGUAACUACCGUCCUG-264
3'- 304-UCGGAAAGACUUGUGUACGUGCCGGUGUAACUACCGUCCUG-264
wt TTR mRNA        V30V-P2:  ACGGCCACAUUGAUGGCAGdTdT
                   V30V-P3:  CACGGCCACAUUGAUGGCAdTdT
                   V30V-P4:  GCACGGCCACAUUGAUGGCdTdT
                   V30V-P5:  UGCACGGCCACAUUGAUGGdTdT
                   V30V-P6:  AUGCACGGCCACAUUGAUGdTdT
                   V30V-P7:  CAUGCACGGCCACAUUGAUdTdT
                   V30V-P8:  ACAUGCACGGCCACAUUGAdTdT
                   V30V-P9:  CACAUGCACGGCCACAUUGdTdT
                   V30V-P10: ACACAUGCACGGCCACAUUdTdT
                   V30V-P11: AACACAUGCACGGCCACAUdTdT
                   V30V-P12: GAACACAUGCACGGCCACAdTdT
                   V30V-P13: UGAACACAUGCACGGCCACdTdT
                   V30V-P14: CUGAACACAUGCACGGCCAdTdT
                   V30V-P15: UCUGAACACAUGCACGGCCdTdT
```

Related U.S. Application Data continuation of application No. 14/667,678, filed on Mar. 25, 2015, now Pat. No. 9,982,259.

(60) Provisional application No. 61/970,319, filed on Mar. 25, 2014.

(51) Int. Cl.
*A61K 31/685* (2006.01)
*A61K 31/713* (2006.01)
*C12N 15/11* (2006.01)

(52) U.S. Cl.
CPC .......... *A61K 31/713* (2013.01); *C12N 15/111* (2013.01); *C12N 2310/14* (2013.01); *C12N 2310/32* (2013.01); *C12N 2310/323* (2013.01); *C12N 2320/32* (2013.01); *C12N 2320/34* (2013.01)

(56) References Cited

U.S. PATENT DOCUMENTS

| | | | |
|---|---|---|---|
| 5,786,359 | A | 7/1998 | Reitz |
| 5,898,031 | A | 4/1999 | Crooke |
| 6,037,176 | A | 3/2000 | Bennett |
| 6,069,132 | A | 5/2000 | Revanker |
| 6,506,559 | B1 | 1/2003 | Fire et al. |
| 6,608,035 | B1 | 8/2003 | Agrawal |
| 6,753,139 | B1 | 6/2004 | Baulcombe |
| 7,056,704 | B2 | 6/2006 | Tuschl |
| 7,078,196 | B2 | 7/2006 | Tuschl |
| 7,459,547 | B2 | 12/2008 | Zamore et al. |
| 7,579,451 | B2 | 8/2009 | Manoharan |
| 7,691,995 | B2 | 4/2010 | Zamore |
| 7,745,608 | B2 | 6/2010 | Manoharan |
| 7,750,144 | B2 | 7/2010 | Zamore |
| 7,786,290 | B2 | 8/2010 | Woppmann |
| 7,915,399 | B2 | 3/2011 | MacLachlan |
| 8,101,584 | B2 | 1/2012 | Kreutzer |
| 8,101,742 | B2 | 1/2012 | Kreutzer |
| 8,258,285 | B2 | 9/2012 | Baulcombe |
| 8,314,227 | B2 | 11/2012 | Wengel |
| 8,362,231 | B2 | 1/2013 | Tuschl |
| 8,420,391 | B2 | 4/2013 | Tuschl |
| 8,546,143 | B2 | 10/2013 | Kreutzer |
| 9,051,570 | B2 | 6/2015 | Wengel |
| 9,365,610 | B2* | 6/2016 | Payne .................. C07J 41/0055 |
| 9,856,475 | B2* | 1/2018 | Tachikawa ............. A61K 9/127 |
| 9,982,259 | B2* | 5/2018 | Tachikawa ............. A61K 9/127 |
| 2002/0086356 | A1 | 7/2002 | Tuschl |
| 2003/0143732 | A1 | 7/2003 | Fosnaugh |
| 2004/0171570 | A1 | 9/2004 | Allerson |
| 2004/0175703 | A1 | 9/2004 | Kreutzer et al. |
| 2004/0192626 | A1 | 9/2004 | McSwiggen et al. |
| 2004/0259247 | A1 | 12/2004 | Tuschl et al. |
| 2004/0261149 | A1 | 12/2004 | Fauquet et al. |
| 2005/0100907 | A1 | 5/2005 | Kreutzer |
| 2005/0107325 | A1 | 5/2005 | Manoharan |
| 2005/0129778 | A1 | 6/2005 | Mulye |
| 2005/0223427 | A1 | 10/2005 | Khvorova |
| 2005/0244858 | A1 | 11/2005 | Rossi et al. |
| 2005/0288244 | A1 | 12/2005 | Manoharan |
| 2006/0122391 | A1 | 6/2006 | Babu |
| 2006/0276635 | A1 | 12/2006 | McSwiggen |
| 2006/0287260 | A1 | 12/2006 | Manoharan |
| 2007/0275914 | A1 | 11/2007 | Manoharan |
| 2009/0093438 | A1 | 4/2009 | McSwiggen |
| 2010/0120893 | A1 | 5/2010 | Baligh et al. |
| 2011/0136233 | A1 | 6/2011 | Quay et al. |
| 2011/0313020 | A1 | 12/2011 | Templin et al. |
| 2012/0120893 | A1 | 5/2012 | Baligh et al. |
| 2012/0225927 | A1 | 9/2012 | Sah |
| 2013/0096289 | A1 | 4/2013 | Wengel |
| 2013/0190383 | A1 | 7/2013 | Vaish et al. |
| 2013/0281510 | A1 | 10/2013 | Ando et al. |
| 2014/0275211 | A1 | 9/2014 | Sah et al. |
| 2014/0315835 | A1 | 10/2014 | Rajeev |
| 2015/0141678 | A1 | 5/2015 | Payne |
| 2015/0307880 | A1 | 10/2015 | Tachikawa |
| 2015/0307881 | A1 | 10/2015 | Tachikawa et al. |

FOREIGN PATENT DOCUMENTS

| | | | |
|---|---|---|---|
| WO | WO-2003004602 | A2 | 1/2003 |
| WO | WO-2003037909 | A1 | 5/2003 |
| WO | WO-03070918 | A2 | 8/2003 |
| WO | WO-03106477 | A1 | 12/2003 |
| WO | WO-2004090105 | A2 | 10/2004 |
| WO | WO-2004090108 | A2 | 10/2004 |
| WO | WO-2004094595 | A2 | 11/2004 |
| WO | WO-2004108897 | A2 | 12/2004 |
| WO | WO-2005089268 | A2 | 9/2005 |
| WO | WO-2005089287 | A2 | 9/2005 |
| WO | WO-2005121372 | A2 | 12/2005 |
| WO | WO-06085987 | A2 | 8/2006 |
| WO | WO-2006112872 | A2 | 10/2006 |
| WO | WO-2007022369 | A2 | 2/2007 |
| WO | WO-2007051303 | A1 | 5/2007 |
| WO | WO-2007056829 | A1 | 5/2007 |
| WO | WO-2008020435 | A2 | 2/2008 |
| WO | WO-08147824 | A2 | 12/2008 |
| WO | WO-2011123468 | A1 | 10/2011 |
| WO | WO-2011133584 | A2 | 10/2011 |
| WO | WO-2014037436 | A1 | 3/2014 |
| WO | WO-2015042564 | A1 * | 3/2015 ........... C12N 15/113 |

OTHER PUBLICATIONS

Bramsen et al., "A large-scale chemical modification screen identifies design rules to generate siRNAs with high activity, high stability and low toxicity," Nucleic Acids Research 2009, vol. 37, No. 9, pp. 2867-2881.

Bramsen, Jesper B., et al., "A screen of chemical modifications identifies position-specific modification by UNA to most potently reduce siRNA off-target effects." Nucleic acids research 38.17 (2010): 5761-5773.

Czauderna, Frank, et al., "Structural variations and stabilising modifications of synthetic siRNAs in mammalian cells." Nucleic acids research 31.11 (2003): 2705-2716.

Elbashir, Sayda M., et al. "Functional anatomy of siRNAs for mediating efficient RNAi in *Drosophila melanogaster* embryo lysate." The EMBO journal 20.23 (2001): 6877-6888.

Habus, "Oligonucleotides Containing Acyclic Nucleoside Analogues with Carbamate Internucleoside Linkages," Nucleosides & Nucleotides, 1995, vol. 14 (9&10), 1853-1859.

Jensen, T. et al., "Unlocked Nucleic Acid (UNA) and UNA Derivatives: Thermal Denaturation Studies;" Nucleic Acids Symposium Series No. 52; Oxford University Press 2008; pp. 133-134.

John Wiley & Sons, Inc.; "IUPAC-IUB Joint Commission on Biochemical Nomenclature Abbreviations and Symbols for the Description of Conformations of Polynucleotide Chains;" Current Protocols in Nucleic Acid Chemistry 2000; pp. A.1C.1-A.1D.3.

Langkjær, Niels, et al., "UNA (unlocked nucleic acid): a flexible RNA mimic that allows engineering of nucleic acid duplex stability." Bioorganic & medicinal chemistry 17.15 (2009): 5420-5425.

Laursen, Maria B., et al., "Utilization of unlocked nucleic acid (UNA) to enhance siRNA performance in vitro and in vivo." Molecular BioSystems 6.5 (2010): 862-870.

Layzer, "In vivo activity of nuclease-resistant siRNAs," RNA (2004), vol. 10, pp. 766-771.

Mangos, M. et al., "Efficient RNase H-Directed Cleavage of RNA Promoted by Antisense DNA or 2'F-ANA Constructs Containing Acyclic Nucleotide Inserts;" Journal of the American Chemical Society 2003; vol. 125; pp. 654-661.

Nielsen, "Oligonucleotide Analogues Containing 4'-C-(Hydroxymethyl)uridine: Synthesis, Evaluation and Mass Spectrometric Analysis," Bioorganic & Medicinal Chemistry, vol. 3, No. 11, pp. 1493-1502, 1995.

(56) References Cited

OTHER PUBLICATIONS

Nielsen, P. et al.; "Synthesis and Evaluation of Oligodeoxynucleotides Containing Acyclic Nucleosides: Introduction of Three Novel Analogues and a Summary;" Bioorganic & Medicinal Chemistry; Elsevier Science Ltd 1995; vol. 3; No. 1; pp. 19-28.

Pandolfi, "Evaluation of Different Types of End-Capping Modifications on the Stability of Oligonucleotides Toward 3'- and 5' Exonucleases," Nucleosides & Nucleotides, 1999, vol. 18 (9), 2051-2069.

Pei et al., "Synthesis of 3'-C-Hydroxymethyl-substituted Pyrimidine and Purine Nucleosides as Potential Anti-Hepatitis C Virus (HCV) Agents," Arch Pharm Res 2009, vol. 31, No. 7, pp. 843-849.

Petersen, "LNA: A versatile tool for therapeutics and genomics," Trends in Biotechnology vol. 21 No. 2 Feb. 2003.

Pfundheller, "Locked Nucleic Acid Synthesis," Chapter 8 in Methods in Molecular Biology, vol. 288: Oligonucleotide Synthesis: Methods and Applications, Edited by: P. Herdewijn, Humana Press, 2005.

pharmabiz.com, Arcturus to present gene knockdown data in non-human primates, showing up to 94% reduction in gene expression with single low dose, dated Oct. 14, 2014.

Snead, Nicholas M., et al., "5' Unlocked nucleic acid modification improves siRNA targeting." Molecular Therapy-Nucleic Acids 2 (2013): 7 Pages.

Thrane, H. et al.; "Novel Linear and Branched Oligodeoxynucleotide Analogues Containing 4'-C-(Hydroxymethyl Thymidine;" Tetrahedron; Elsevier Science Ltd 1995; vol. 51; No. 37; pp. 10389-10402.

Vaish, Narendra, et al., "Improved specificity of gene silencing by siRNAs containing unlocked nucleobase analogs." Nucleic acids research 39.5 (2010): 1823-1832.

Werk, Denise, et al., "Application of small interfering RNAs modified by unlocked nucleic acid (UNA) to inhibit the heart-pathogenic coxsackievirus B3." FEBS letters 584.3 (2010): 591-598.

* cited by examiner

V30M TTR mRNA

3'-304-UCGGAAAGACUUGUGUACGUACCGGUGUAACUACGUCCUG-264   SEQ ID NOS: 103-118

3'-304-UCGGAAAGACUUGUGUACGUACCGGUGUAACUACGUCCUG-264 wt TTR mRNA

V30V-P2:   ACGGCCACAUUGAUGGCAGdTdT
V30V-P3:   CACGGCCACAUUGAUGGCAdTdT
V30V-P4:   GCACGGCCACAUUGAUGGCdTdT
V30V-P5: UGCACGGCCACAUUGAUGGdTdT
V30V-P6:   AUGCACGGCCACAUUGAUGdTdT
V30V-P7:   CAUGCACGGCCACAUUGAUdTdT
V30V-P8:   ACAUGCACGGCCACAUUGAdTdT
V30V-P9:   CACAUGCACGGCCACAUUGdTdT
V30V-P10: ACACAUGCACGGCCACAUUdTdT
V30V-P11: AACACAUGCACGGCCACAUdTdT
V30V-P12: GAACACAUGCACGGCCACAdTdT
V30V-P13: UGAACACAUGCACGGCCACdTdT
V30V-P14: CUGAACACAUGCACGGCCAdTdT
V30V-P15: UCUGAACACAUGCACGGCCdTdT

FIG. 1

```
                                                                    284  SEQ ID NOS: 103, 104, 108, 112, 117, 118
V30M TTR mRNA
          3'-304-UCGGAAAGACUUGUGUACCGGUGUAACUACCGUCCUG-264
          3'-304-UCGGAAAGACUUGUGUACCGGUGUAACUACCGUCCUG-264
wt TTR mRNA
         V30V-P5:  UGCACGGCCACAUUGAUGGdTdT
         V30V-P9:  CACAUGCACGGCCACAUUGAUGGdTdT
         V30V-P14: CUGAACACAUGCACGGCCAdTdT
         V30V-P15: UCUGAACACAUGCACGGCCCdTdT
                                                                    SEQ ID NOS: 119-122
         V30M-P5:  UGCAUGGCCACAUUGAUGGdTdT
         V30M-P9:  CACAUGCAUGGCCACAUUGAUGGdTdT
         V30M-P14: CUGAACACAUGCAUGGCCAdTdT
         V30M-P15: UCUGAACACAUGCAUGGCCCdTdT
```

FIG. 3

| siRNA ID | SS ID | seq. (5'->3') | AS ID | seq. (5'->3') |
|---|---|---|---|---|
| P15 | P15SS | GGCCAUGCAUGUGCAUGUUCAGAdTdT | P15AS | UCUGAACACAUGCAUGGCCdTdT |
| P15U6 | P15USS | ĞGCCAUGCAUGUGCAUGUUCAGAÜmU | P15U6AS | UCUGAÃCACAUGCAUGGCCÜmU |
| P15U7 | P15USS | ĞGCCAUGCAUGUGCAUGUUCAGAÜmU | P15U7AS | UCUGAAĈACAUGCAUGGCCÜmU |
| P15U14 | P15USS | ĞGCCAUGCAUGUGCAUGUUCAGAÜmU | P15U14AS | UCUGAACACAUGCÃUGGCCÜmU |
| P15U15 | P15USS | ĞGCCAUGCAUGUGCAUGUUCAGAÜmU | P15U15AS | UCUGAACACAUGCAÜGGCCÜmU |
| P15U16 | P15USS | ĞGCCAUGCAUGUGCAUGUUCAGAÜmU | P15U16AS | UCUGAACACAUGCAUĞGCCÜmU |

SEQ ID NOS: 123-128 (SS); SEQ ID NOS: 129-134 (AS)

FIG. 6

| siRNA ID | SS ID | seq. (5' -> 3') | AS ID | seq. (5' -> 3') |
|---|---|---|---|---|
| P16 | P16SS | GCCAUGCAUGUGUUCAGAAdTdT | P16AS | UUCUGAACACAUGCAUGGCdTdT |
| P16U6 | P16USS | ĞCCAUGCAUGUGUUCAGAAŬmU | P16U6AS | UUCUGĂACACAUGCAUGGCŬmU |
| P16U7 | P16USS | ĞCCAUGCAUGUGUUCAGAAŬmU | P16U7AS | UUCUGAĂCACAUGCAUGGCŬmU |
| P16U15 | P16USS | ĞCCAUGCAUGUGUUCAGAAŬmU | P16U15AS | UUCUGAACACAUGCĂUGGCŬmU |
| P16U16 | P16USS | ĞCCAUGCAUGUGUUCAGAAŬmU | P16U16AS | UUCUGAACACAUGCAŬGGCŬmU |
| P16U17 | P16USS | ĞCCAUGCAUGUGUUCAGAAŬmU | P16U17AS | UUCUGAACACAUGCAUĞGCŬmU |

SEQ ID NOS: 135-140 (SS) ; SEQ ID NOS: 141-146 (AS)

FIG. 8

SEQUENCE LISTING

```
<160> NUMBER OF SEQ ID NOS: 146

<210> SEQ ID NO 1
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 1
nnnnnnnnnn nnnnnnnnnn nn                                              22

<210> SEQ ID NO 2
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: Any natural, non-natural, modified, or
      chemically-modified nucleotide; may or may not be modified
      based on a propane-1,2,3-tri-yl-trisoxy structure

<400> SEQUENCE: 2
nnnnnnnnnn nnnnnnnnnn n                                              21

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ggccaugcau guguucagau u                                              21

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
ucugaacaca ugcauggccu u                                              21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ggccaugcau guguucagau u                                              21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ucugaacaca ugcauggccu u                                              21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
ggccaugcau guguucagau u                                              21
```

```
<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ucugaacaca ugcauggccu u                                               21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
ggccaugcau guguucagau u                                               21

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
ucugaacaca ugcauggccu u                                               21

<210> SEQ ID NO 11
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
ggccaugcau guguucagau u                                               21

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
ucugaacaca ugcauggccu u                                               21

<210> SEQ ID NO 13
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
gccaugcaug uguucagaau u                                               21

<210> SEQ ID NO 14
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
uucugaacac augcauggcu u                                                 21

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
gccaugcaug uguucagaau u                                                 21

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
uucugaacac augcauggcu u                                                 21

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
gccaugcaug uguucagaau u                                                 21

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
uucugaacac augcauggcu u                                                 21

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
gccaugcaug uguucagaau u                                                 21

<210> SEQ ID NO 20
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
uucugaacac augcauggcu u                                              21

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
gccaugcaug uguucagaau u                                              21

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
uucugaacac augcauggcu u                                              21

<210> SEQ ID NO 23
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
auguaaccaa gaguauucca uuuuuac                                        27

<210> SEQ ID NO 24
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
auguaaccaa gaguauucca uuuuuac                                        27

<210> SEQ ID NO 25
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
auguaaccaa gaguauucca uuuuuac                                        27

<210> SEQ ID NO 26
<211> LENGTH: 27
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 26
auguaaccaa gaguauucca uuuuuac                                              27

<210> SEQ ID NO 27
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
auguaaccaa gaguauucca uuuuuac                                              27

<210> SEQ ID NO 28
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
auguaaccaa gaguauucca uuuuuac                                              27

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 29
guaaccaaga guauuccauu uuuacta                                              27

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 30
guaaccaaga guauuccauu uuuacta                                              27

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 31
guaaccaaga guauuccauu uuuacta                                           27

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 32
guaaccaaga guauuccauu uuuacta                                           27

<210> SEQ ID NO 33
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
guaaccaaga guauuccauu uuuacua                                           27

<210> SEQ ID NO 34
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
guaaccaaga guauuccauu uuuacua                                           27

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 35
guaaccaaga guauuccaut t                                                 21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 36
guaaccaaga guauuccaut t                                                 21
```

```
<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 37
guaaccaaga guauuccaut t                                              21

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
guaaccaaga guauuccauu u                                              21

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
guaaccaaga guauuccauu u                                              21

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
guaaccaaga guauuccauu u                                              21

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
guaaccaaga guauuccauu u                                              21

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
guaaccaaga guauuccauu u                                              21
```

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
guaaccaaga guauuccauu u                                          21

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
guaaccaaga guauuccauu u                                          21

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
guaaccaaga guauuccauu u                                          21

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
guaaccaaga guauuccauu u                                          21

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
auguaaccaa gaguauuccu u                                          21

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
auguaaccaa gaguauuccu u                                          21

```
<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
auguaaccaa gaguauuccu u                                                   21

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
auguaaccaa gaguauuccu u                                                   21

<210> SEQ ID NO 51
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
agaguauucc auuuuuacuu                                                     20

<210> SEQ ID NO 52
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
agaguauucc auuuuuacuu                                                     20

<210> SEQ ID NO 53
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
agaguauucc auuuuuacuu                                                     20

<210> SEQ ID NO 54
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
agaguauucc auuuuuacuu                                                     20
```

```
<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
gacugguauu ugugucugau u                                              21

<210> SEQ ID NO 56
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
gacugguauu ugugucugau u                                              21

<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
gacugguauu ugugucugau u                                              21

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
gacugguauu ugugucugau u                                              21

<210> SEQ ID NO 59
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
uguaaccaag aguauuccau u                                              21

<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
uaaccaagag uauuccauuu u                                              21

<210> SEQ ID NO 61
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
ccaagaguau uccauuuuuu u                                              21

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
ccaagaguau uccauuuuuu u                                              21

<210> SEQ ID NO 63
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
guaaaaaugg aauacucuug guuacau                                        27

<210> SEQ ID NO 64
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
guaaaaaugg aauacucuug guuacau                                        27

<210> SEQ ID NO 65
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
guaaaaaugg aauacucuug guuacau                                        27

<210> SEQ ID NO 66
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 66
guaaaaaugg aauacucuug guuacau                                        27

<210> SEQ ID NO 67
<211> LENGTH: 27
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 67
guaaaaaugg aauacucuug guuacau                                              27

<210> SEQ ID NO 68
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 68
guaaaaaugg aauacucuug guuacau                                              27

<210> SEQ ID NO 69
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 69
uaguaaaaau ggaauacucu ugguuac                                              27

<210> SEQ ID NO 70
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
uaguaaaaau ggaauacucu ugguuac                                              27

<210> SEQ ID NO 71
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
uaguaaaaau ggaauacucu ugguuac                                              27

<210> SEQ ID NO 72
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
uaguaaaaau ggaauacucu ugguuac                                              27

<210> SEQ ID NO 73
<211> LENGTH: 27
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 73
uaguaaaaau ggaauacucu ugguuac                                       27

<210> SEQ ID NO 74
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
uaguaaaaau ggaauacucu ugguuac                                       27

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 75
auggaauacu cuugguuact t                                             21

<210> SEQ ID NO 76
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
auggaauacu cuugguuacu u                                             21

<210> SEQ ID NO 77
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
auggaauacu cuugguuacu u                                             21

<210> SEQ ID NO 78
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 78
auggaauacu cuugguuacu u                                             21

<210> SEQ ID NO 79
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 79
auggaauacu cuugguuacu u                                                 21

<210> SEQ ID NO 80
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
auggaauacu cuugguuacu u                                                 21

<210> SEQ ID NO 81
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
auggaauacu cuugguuacu u                                                 21

<210> SEQ ID NO 82
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
auggaauacu cuugguuaca u                                                 21

<210> SEQ ID NO 83
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
auggaauacu cuugguuacu u                                                 21

<210> SEQ ID NO 84
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 84
auggaauacu cuugguuacu u                                                 21

<210> SEQ ID NO 85
<211> LENGTH: 21
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
auggaauacu cuugguuacu u                                              21

<210> SEQ ID NO 86
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
auggaauacu cuugguuacu u                                              21

<210> SEQ ID NO 87
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
ggaauacucu ugguuacauu u                                              21

<210> SEQ ID NO 88
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
ggaauacucu ugguuacauu u                                              21

<210> SEQ ID NO 89
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
ggaauacucu ugguuacauu u                                              21

<210> SEQ ID NO 90
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
ggaauacucu ugguuacauu u                                              21

<210> SEQ ID NO 91
<211> LENGTH: 20
<212> TYPE: RNA

```
<213> ORGANISM: Artificial Sequence
<220> FEATURE:
<223> OTHER INFORMATION: Description of Artificial Sequence: Synthetic
      oligonucleotide

<400> SEQUENCE: 91
aguaaaaaug gaauacucuu                                                    20

<210> SEQ ID NO 92
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
aguaaaaaug gaauacucuu                                                    20

<210> SEQ ID NO 93
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
aguaaaaaug gaauacucuu                                                    20

<210> SEQ ID NO 94
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
aguaaaaaug gaauacucuu                                                    20

<210> SEQ ID NO 95
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
ucagacacaa auaccagucc a                                                  21

<210> SEQ ID NO 96
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
ucagacacaa auaccagucc a                                                  21

<210> SEQ ID NO 97
<211> LENGTH: 21
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 97
ucagacacaa auaccagucc a                                              21

<210> SEQ ID NO 98
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
ucagacacaa auaccagucc a                                              21

<210> SEQ ID NO 99
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
uggaauacuc uugguuacau u                                              21

<210> SEQ ID NO 100
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
aauggaauac ucuugguuau u                                              21

<210> SEQ ID NO 101
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
aaaaauggaa uacucuuggu u                                              21

<210> SEQ ID NO 102
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
aaaaauggaa uacucuuggu u                                              21

<210> SEQ ID NO 103
<211> LENGTH: 41
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 103
guccugccau caauguggcc augcaugugu ucagaaaggc u                          41

<210> SEQ ID NO 104
<211> LENGTH: 41
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
guccugccau caauguggcc gugcaugugu ucagaaaggc u                          41

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 105
acggccacau ugauggcagt t                                                21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 106
cacggccaca uugauggcat t                                                21

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 107
gcacggccac auugauggct t                                                21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 108
ugcacggcca cauugauggt t                                                21

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 109
augcacggcc acauugaugt t                                                21

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 110
caugcacggc cacauugaut t                                                21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 111
acaugcacgg ccacauugat t                                                21

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 112
cacaugcacg gccacauugt t                                                21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 113
acacaugcac ggccacauut t                                              21

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 114
aacacaugca cggccacaut t                                              21

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 115
gaacacaugc acggccacat t                                              21

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 116
ugaacacaug cacggccact t                                              21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 117
cugaacacau gcacggccat t                                              21

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 118
ucugaacaca ugcacggcct t                                              21

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 119
ugcauggcca cauugauggt t                                              21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 120
cacaugcaug gccacauugt t                                              21

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 121
cugaacacau gcauggccat t                                              21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 122
ucugaacaca ugcauggcct t                                              21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 123
ggccaugcau guguucagat t                                              21

<210> SEQ ID NO 124
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
ggccaugcau guguucagau u                                              21

<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
ggccaugcau guguucagau u                                              21

<210> SEQ ID NO 126
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
ggccaugcau guguucagau u                                              21

<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
ggccaugcau guguucagau u                                              21

<210> SEQ ID NO 128
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
ggccaugcau guguucagau u                                              21

<210> SEQ ID NO 129
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 129
ucugaacaca ugcauggcct t                                                    21

<210> SEQ ID NO 130
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
ucugaacaca ugcauggccu u                                                    21

<210> SEQ ID NO 131
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
ucugaacaca ugcauggccu u                                                    21

<210> SEQ ID NO 132
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
ucugaacaca ugcauggccu u                                                    21

<210> SEQ ID NO 133
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
ucugaacaca ugcauggccu u                                                    21

<210> SEQ ID NO 134
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
ucugaacaca ugcauggccu u                                                    21

<210> SEQ ID NO 135
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 135
gccaugcaug uguucagaat t                                              21

<210> SEQ ID NO 136
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
gccaugcaug uguucagaau u                                              21

<210> SEQ ID NO 137
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
gccaugcaug uguucagaau u                                              21

<210> SEQ ID NO 138
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
gccaugcaug uguucagaau u                                              21

<210> SEQ ID NO 139
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
gccaugcaug uguucagaau u                                              21

<210> SEQ ID NO 140
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
gccaugcaug uguucagaau u                                              21

<210> SEQ ID NO 141

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 141
uucugaacac augcauggct t                                              21

<210> SEQ ID NO 142
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
uucugaacac augcauggcu u                                              21

<210> SEQ ID NO 143
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
uucugaacac augcauggcu u                                              21

<210> SEQ ID NO 144
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
uucugaacac augcauggcu u                                              21

<210> SEQ ID NO 145
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
uucugaacac augcauggcu u                                              21

<210> SEQ ID NO 146
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
uucugaacac augcauggcu u                                              21
```

THERAPEUTIC OLIGOMERS FOR TREATING AMYLOIDOSIS

SEQUENCE LISTING

This application includes a Sequence Listing submitted electronically herewith as an ASCII file created on Dec. 31, 2017, named ARC1253US_SL.txt, which is 37,882 bytes in size, and is hereby incorporated by reference in its entirety.

BACKGROUND OF THE INVENTION

The presence of certain diseases appears to correlate with expression of a mutant allele. For example, amyloidosis can be correlated to certain transthyretin (TTR) mutations. In such cases, it is desirable to selectively silence expression of the mutant allele, while maintaining expression of the wild-type variant.

Amyloidosis related to transthyretin (ATTR) involves the depositing of amyloid fibril proteins in various organs and tissues, including the peripheral, autonomic, and central nervous systems. Transthyretin (TTR) is a secreted thyroid hormone-binding protein that binds and transports retinol binding protein, and serum thyroxine in plasma and cerebrospinal fluid.

The pathology of ATTR may include many TTR mutations. Symptoms of ATTR often include neuropathy and/or cardiomyopathy. Peripheral neuropathy can begin in the lower extremities, with sensory and motor neuropathy, and can progress to the upper extremities. Autonomic neuropathy can be manifest by gastrointestinal symptoms and orthostatic hypotension.

Patients with TTR gene Val-30-Met, the most common mutation, have normal echocardiograms. However, they may have conduction system irregularities and need a pacemaker. The ATTR V30M variant can cause lower extremity weakness, pain, and impaired sensation, as well as autonomic dysfunction. Vitreous and opaque amyloid deposits can be characteristic of ATTR.

Survival upon onset of ATTR may be from five to fifteen years. The major treatment for ATTR amyloidosis is liver transplantation, which removes the major source of variant TTR production and replaces it with normal TTR. Liver transplantation slows disease progression and some improvement in autonomic and peripheral neuropathy can occur.

There is currently no pharmacological therapy that can undo the formation of TTR amyloid.

There is a continuing need for therapeutics for ATTR and other amyloid-related diseases.

There is a long-standing need for gene silencing agents that can selectively downregulate a disease-related allele.

There is also a need for active agents that can provide efficient and specific knockdown of TTR.

BRIEF SUMMARY

This invention relates to the fields of biopharmaceuticals and therapeutics based on allele selective gene silencing. More particularly, this invention relates to methods for treating transthyretin-related amyloidosis with UNA oligomers capable of allele-selective knockdown of transthyretin.

This invention provides UNA oligomers for selectively inhibiting V30M TTR expression, which can be used in treating amyloidosis. The UNA oligomers can have a first strand and a second strand, each of the strands being 19-29 monomers in length, the monomers being UNA monomers and nucleic acid monomers. Embodiments include pharmaceutical compositions and methods for treating or preventing TTR-related amyloidosis by administering a UNA oligomer to a subject.

Embodiments of this invention include the following:

A UNA oligomer for selectively inhibiting V30M TTR expression, the oligomer comprising a first strand and a second strand, each of the strands being 19-29 monomers in length, the monomers comprising UNA monomers and nucleic acid monomers, wherein the oligomer has a duplex structure of from 14 to 29 monomers in length.

The UNA oligomer above, wherein the second strand has at least one UNA monomer in the duplex region. The UNA oligomer above, wherein the at least one UNA monomer in the second strand is at any one of positions 2-8 from the 5' end. The UNA oligomer above, wherein the at least one UNA monomer in the second strand is at any one of positions 9-18 from the 5' end. The UNA oligomer above, wherein the at least one UNA monomer in the second strand is at position 6, 7, 15, 16 or 17 from the 5' end.

The UNA oligomer above, wherein the oligomer has an IC50 for reducing V30M TTR expression of less than 20 pM.

The UNA oligomer above, wherein the oligomer has a selectivity ratio of at least 10, wherein the selectivity ratio is the ratio of the IC50 for reducing wild type TTR expression to the IC50 for reducing V30M TTR expression. The UNA oligomer above, wherein the oligomer has a selectivity ratio of at least 20. The UNA oligomer above, wherein the oligomer has a selectivity ratio in vitro of at least 50.

The UNA oligomer above, wherein the oligomer selectively inhibits V30M TTR expression in vivo. The UNA oligomer above, wherein the oligomer selectively inhibits V30M TTR expression ex vivo.

The UNA oligomer above, comprising at least one nucleic acid monomer that is base-modified, sugar-modified, or linkage modified.

A pharmaceutical composition comprising a UNA oligomer above and a pharmaceutically acceptable carrier. The pharmaceutical composition above, comprising a lipid formulation. The pharmaceutical composition above, comprising one or more lipids selected from cationic lipids, anionic lipids, sterols, pegylated lipids, and any combination of the foregoing. The pharmaceutical composition above, wherein the composition is substantially free of liposomes. The pharmaceutical composition above, wherein the composition contains liposomes.

A method for treating or preventing TTR-related amyloidosis, comprising administering to a subject in need an effective amount of a UNA oligomer above. The method above, wherein the TTR-related amyloidosis is ATTR. The method above, wherein the subject is human. The method above, wherein the subject comprises a V30M gene. The method above, wherein the method selectively reduces V30M TTR in the subject. The method above, wherein the administering is local or systemic. The method above, wherein the administering is intravenous, subcutaneous, pulmonary, intramuscular, intraperitoneal, dermal, or oral. The method above, wherein the method selectively reduces V30M TTR in the subject by at least 10% greater than control. The method above, wherein the effective amount is a dose of from 0.001 to 50.0 mg/kg.

The method above, wherein TTR mRNA expression is reduced for at least 5 days. The method above, wherein the method reduces peripheral neuropathy or autonomic neuropathy in the subject. The method above, wherein the administration does not result in an inflammatory response.

A method for inhibiting expression of a TTR gene in a cell, comprising treating the cell with a UNA oligomer above.

A method for inhibiting expression of a TTR gene in a mammal, comprising administering to the mammal a UNA oligomer above.

A pharmaceutical composition comprising a UNA oligomer targeted to TTR and a pharmaceutically acceptable carrier. The pharmaceutical composition may contain a UNA oligomer having a first strand and a second strand, each of the strands being 19-29 monomers in length, the monomers comprising UNA monomers and nucleic acid monomers, wherein the oligomer has a duplex structure of from 14 to 29 monomers in length. A contiguous portion of the second strand may have a sequence according to the entire sequence of one of SEQ ID NOs:63-102.

The carrier may be a lipid formulation, and may contain liposomes that encapsulate the UNA oligomer.

In some embodiments, the pharmaceutical composition, upon administering a single intravenous dose to a primate, may reduce TTR protein in the primate by at least 90% after 20 days.

In some embodiments, the pharmaceutical composition, upon administering a single intravenous dose to a primate, may reduce TTR protein in the primate by at least 70% for a period of at least 20 days.

In certain embodiments, the pharmaceutical composition, upon administering a single intravenous dose to a primate, may reduce TTR protein in the primate by at least 50% for a period of at least 30 days.

This invention further contemplates methods for treating or preventing TTR-related amyloidosis in a primate in need, by administering to the primate an effective amount of a pharmaceutical composition comprising a UNA oligomer targeted to TTR and a pharmaceutically acceptable carrier. The primate may be a human.

A use of a formulation comprising nanoparticles that encapsulate a UNA oligomer for treating or preventing TTR-related amyloidosis in a primate.

The use above, wherein upon administering a single dose of the formulation to the primate, the TTR protein in the primate is reduced by at least 90% after 20 days.

The use above, wherein upon administering a single dose of the formulation to the primate, the TTR protein in the primate is reduced by at least 70% for a period of at least 10 days.

The use above, wherein upon administering a single dose of the formulation to the primate, the TTR protein in the primate is reduced by at least 70% for a period of at least 20 days.

The use above, wherein upon administering a single dose of the formulation to the primate, the TTR protein in the primate is reduced by at least 50% for a period of at least 30 days.

BRIEF DESCRIPTION OF THE DRAWINGS

FIG. 1 shows the single nucleotide polymorph (SNP) that exists at position 284 in the V30M mutation mRNA, as compared to the wild type (WT) TTR mRNA. Conventional siRNAs that are complementary to the WT mRNA can be tiled around position 284.

FIG. 3 shows that conventional siRNAs that are complementary to the V30M mRNA can be tiled around position 284. Four conventional siRNA variations, namely V30M-P5, V30M-P9, V30M-P14, and V30M-P15, were prepared. Also, as shown in FIG. 3, two reporter variants, V30V and V30M, each bearing nucleotide sequence 264 to 304 of human TTR, V30V being without the point mutation at position 284, and V30M containing the point mutation at position 284, were prepared and used in the PSICHECK reporter system in the 3'-UTR region of Luciferase gene.

FIG. 6 shows the structure of UNA oligomers that were effective in silencing V30M TTR, as measured in the PSI-CHECK reporter assay. Each of the UNA oligomer embodiments, P15U6, P15U7, P15U14, P15U15, and P15U16, contained four UNA monomers. In each UNA oligomer, a first UNA monomer was located at the 5' end of the first strand, also called the passenger strand. In each UNA oligomer, the second strand, also called the guide strand, formed a duplex region of 19 monomers length with the first strand. Each UNA oligomer had a duplex region of 19 monomers, and a two-monomer overhang at each end. In each UNA oligomer, a second UNA monomer was located at the 3' end of the first strand, in the $20^{th}$ position, which is in an overhang portion. In each UNA oligomer, a third UNA monomer was located at the 3' end of the second strand, in the $20^{th}$ position, which is in an overhang portion. In the UNA oligomer embodiments, P15U6, P15U7, P15U14, P15U15, and P15U16, a fourth UNA monomer was located in the second strand at positions 6, 7, 14, 15 and 16, respectively, counting from the 5' end of the second strand.

FIG. 7 shows the surprising and unexpected result that the selectivity of the UNA oligomers, P15U6, P15U7, P15U15, and P15U16, against V30M over V30V was substantially greater than for the conventional siRNA V30M-P15. In particular, the selectivity of UNA oligomer P15U6 against V30M over V30V was 24, meaning that the IC50 of UNA oligomer P15U6 against V30M (37.6 pM) was 24 times lower than the IC50 of UNA oligomer P15U6 against V30V (919.9 pM). This selectivity was advantageously 4-fold superior to the selectivity of 5.6 shown above in FIG. 5 for the conventional siRNA.

FIG. 8 shows the structure of UNA oligomers that were effective in silencing V30M TTR, as measured in the PSI-CHECK reporter assay. Each of the UNA oligomer embodiments, P16U6, P16U7, P16U15, P16U16, and P16U17, contained four UNA monomers. In each UNA oligomer, a first UNA monomer was located at the 5' end of the first strand, also called the passenger strand. In each UNA oligomer, the second strand, also called the guide strand, formed a duplex region of 19 monomers length with the first strand. Each UNA oligomer had a duplex region of 19 monomers, and a two-monomer overhang at each end. In each UNA oligomer, a second UNA monomer was located at the 3' end of the first strand, in the 20$^{th}$ position, which is in an overhang portion. In each UNA oligomer, a third UNA monomer was located at the 3' end of the second strand, in the 20$^{th}$ position, which is in an overhang portion. In the UNA oligomer embodiments, P16U6, P16U7, P16U15, P16U16, and P16U17, a fourth UNA monomer was located in the second strand at positions 6, 7, 15, 16 and 17, respectively, counting from the 5' end of the second strand.

FIG. 9 shows the surprising and unexpected result that the selectivity of the UNA oligomers, P16U6, P16U7, P16U15, and P16U16, against V30M over V30V was substantially greater than for the conventional siRNA V30M-P16. In particular, the selectivity of UNA oligomer P16U6 against V30M over V30V was 23, meaning that the IC50 of UNA oligomer P16U6 against V30M (92.4 pM) was 23 times lower than the IC50 of UNA oligomer P16U6 against V30V (2119 pM). This selectivity was advantageously 4-fold superior to the selectivity of 5.6 shown above in FIG. 5 for the conventional siRNA.

FIG. 10 (right) shows the surprising and unexpected result that the IC50 of UNA oligomer P16U6 against V30M (92.4 pM) was 23 times lower than the IC50 of UNA oligomer P16U6 against V30V (2119 pM). This selectivity was advantageously 4-fold superior to the selectivity of 5.6 shown above in FIG. 5 for the conventional siRNA.

DETAILED DESCRIPTION OF THE INVENTION

Figure 2:
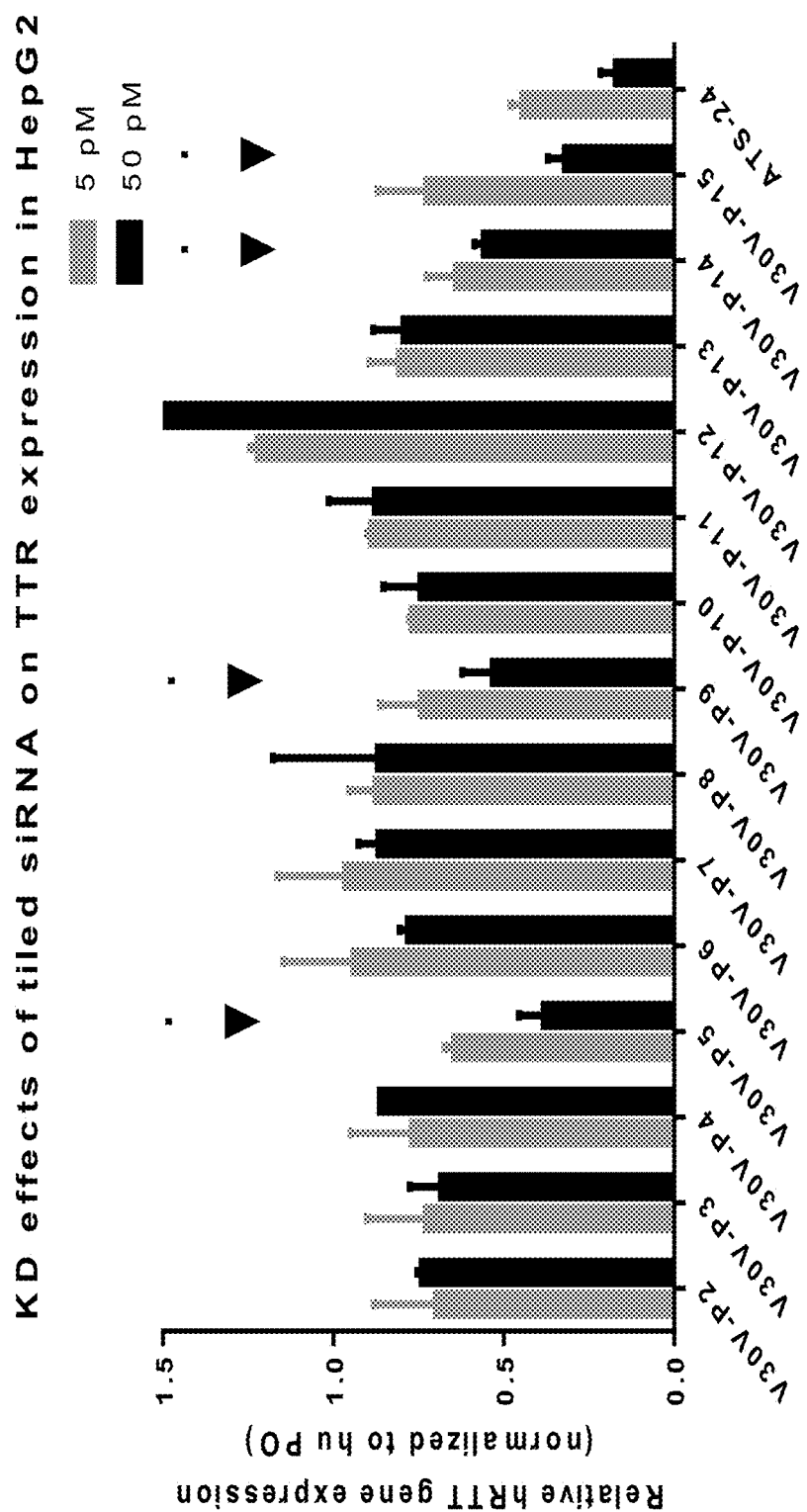
FIG. 2 shows that the conventional siRNAs complementary to the WT mRNA have limited activity in silencing WT TTR gene, as measured by TTR knockdown in HepG2 cells. Positions 5, 9, 14 and 15, indicated by arrows, appear to be more accessible to silencing than other positions.

This invention provides UNA oligomers for selectively inhibiting V30M TTR expression. The UNA oligomers of this invention can be used as therapeutics for treating amyloidosis. In particular, this invention provides UNA oligomers, compositions and methods for treating transthyretin-related amyloidosis.

The UNA oligomers can have a first strand and a second strand, each of the strands being 19-29 monomers in length, the monomers being UNA monomers and nucleic acid monomers. Embodiments of this invention include pharmaceutical compositions and methods for treating or preventing TTR-related amyloidosis by administering a UNA oligomer to a subject.

The UNA oligomers of this invention are capable of allele-specific knockdown of transthyretin.

In some embodiments, UNA oligomers are provided for treating amyloidosis related to transthyretin (ATTR). The UNA oligomers of this invention can reduce the depositing of amyloid fibril proteins in various organs and tissues, including the peripheral, autonomic, and central nervous systems.

In certain aspects, this invention provides therapeutics for ATTR and related amyloid-related diseases.

Aspects of this invention include UNA oligomers that can be used for treating clinical features of ATTR amyloidosis, including neuropathy and/or cardiomyopathy.

In some embodiments, UNA oligomers of this invention are targeted to one mutation Val-30-Met TTR.

This invention can provide a pharmacological therapy that can undo the formation of TTR amyloid.

100551 *Homo sapiens* transthyretin (TTR) mRNA is found at NCBI Reference Sequence: NM_000371.3.

In some aspects, a pharmaceutical composition of this invention can provide an unexpectedly advantageous duration of action. In certain embodiments, upon administering a single dose of a pharmaceutical composition containing a UNA oligomer of this invention, the TTR protein in a subject may be reduced by at least 90% after 20 days.

In further embodiments, upon administering a single dose of a pharmaceutical composition containing a UNA oligomer of this invention, the TTR protein in a subject may be reduced by at least 70% for a period of at least 20 days.

In additional embodiments, upon administering a single dose of a pharmaceutical composition containing a UNA oligomer of this invention, the TTR protein in a subject may be reduced by at least 50% for a period of at least 30 days.

A subject can be a primate, a human, or other mammal.

UNA Oligomers

The UNA oligomers of this invention can be used for inhibiting V30M TTR expression.

A UNA oligomer of this invention the oligomer may have a first strand and a second strand, each of the strands being 19-29 monomers in length.

The monomers of a UNA oligomer can include UNA monomers and nucleic acid monomers A UNA oligomer can be a duplex structure of from 14 to 29 monomers in length.

In some embodiments, the second strand of a UNA oligomer can have at least one UNA monomer in the duplex region. In certain embodiments, a UNA oligomer can have at least one UNA monomer in the second strand at any of positions 6, 7, 15, 16 or 17 from the 5' end in the duplex region.

A UNA oligomer of this invention may have any number of UNA monomers within its total length.

A UNA oligomer can include a nucleic acid monomer that is base-modified, sugar-modified, or linkage modified.

Embodiments of this invention further provide UNA oligomers that selectively inhibit V30M TTR expression.

In certain embodiments, a UNA oligomer has an IC50 for reducing V30M TTR expression in vitro of less than 20 pM.

In further embodiments, a UNA oligomer can have a selectivity ratio in vitro of at least 5. The selectivity ratio is the ratio of the IC50 for reducing V30M TTR expression to the IC50 for reducing wild type TTR expression. The selectivity ratio of a UNA oligomer of this invention can range from 2 to 1000. In certain embodiments, the selectivity ratio of a UNA oligomer is at least 2, or at least 5, or at least 10, or at least 30, or at least 30, or at least 50, or at least 100.

In some aspects, a UNA oligomer of this invention can selectively inhibit V30M TTR expression in vivo.

In certain aspects, a UNA oligomer of this invention can selectively inhibit V30M TTR expression ex vivo.

A UNA oligomer is an active pharmaceutical molecule being a chain composed of monomers, also called an oligomer. The monomers of the oligomer can include UNA monomers and other nucleic acid monomers.

The UNA monomers are novel, synthetic molecules that can be attached in a chain to form an oligomer.

The nucleic acid monomers can be naturally-occurring nucleotides, modified naturally-occurring nucleotides, or certain non-naturally-occurring nucleotides.

A UNA oligomer of this invention is a synthetic, pharmacologically active molecule and can be used in the treatment of a condition or disease.

A UNA oligomer of this disclosure can be a double stranded oligomer. Each strand of the double stranded oligomer can be composed of UNA monomers along with a number of nucleic acid monomers for a total length of 19 to 29 monomers.

A UNA oligomer of this invention can contain one or more UNA monomers in any strand. The UNA monomers can be in a single strand, or in either strand of a double stranded UNA oligomer, or in both strands of a double stranded UNA oligomer.

UNA Monomers

UNA monomers are small organic molecules based on a propane-1,2,3-tri-yl-trisoxy structure as shown below:

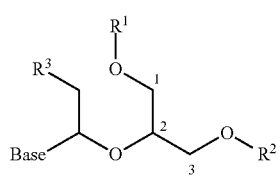

UNA MONOMER where $R^1$ and $R^2$ are H, and $R^1$ and $R^2$ can be phosphodiester linkages, Base can be a nucleobase, and $R^3$ is a functional group described below.

In another view, the UNA monomer main atoms can be drawn in IUPAC notation as follows:

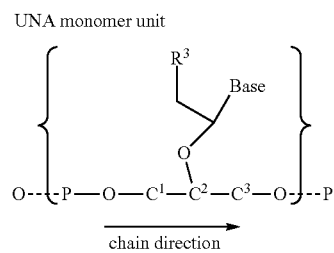

UNA monomer unit where the direction of progress of the oligomer chain is from the 1-end to the 3-end of the propane residue.

Examples of a nucleobase include uracil, thymine, cytosine, 5-methylcytosine, adenine, guanine, inosine, and natural and non-natural nucleobase analogues.

In general, because the UNA monomers are not nucleotides, they can exhibit at least four forms in an oligomer. First, a UNA monomer can be an internal monomer in an oligomer, where the UNA monomer is flanked by other monomers on both sides. In this form, the UNA monomer can participate in base pairing when the oligomer is a duplex, for example, and there are other monomers with nucleobases in the duplex.

Examples of UNA monomer as internal monomers flanked at both the propane-1-yl position and the propane-3-yl position, where $R^3$ is —OH, are shown below.

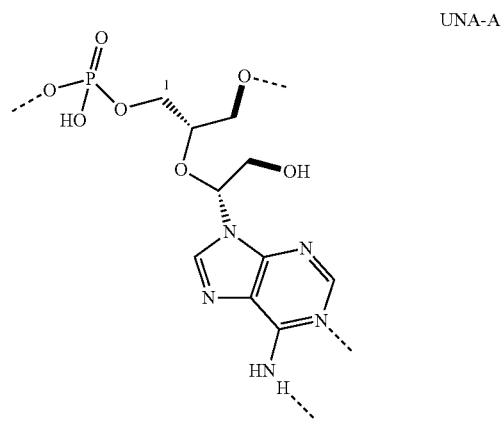

UNA-A

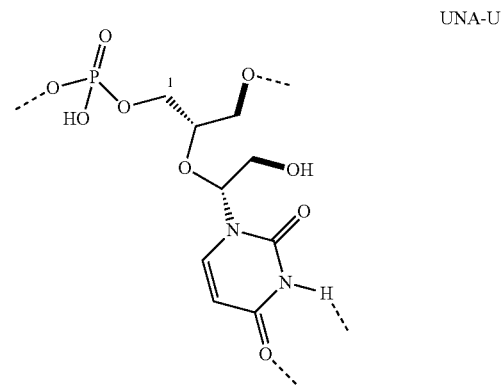

UNA-U

-continued

UNA-C
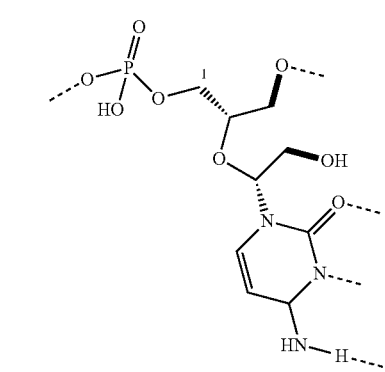

UNA-G
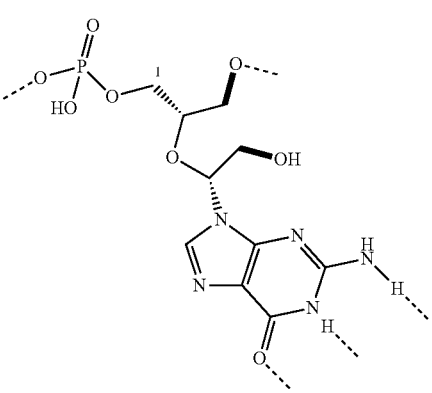

Second, a UNA monomer can be a monomer in an overhang of an oligomer duplex, where the UNA monomer is flanked by other monomers on both sides. In this form, the UNA monomer does not participate in base pairing. Because the UNA monomers are flexible organic structures, unlike nucleotides, the overhang containing a UNA monomer will be a flexible terminator for the oligomer.

A UNA monomer can be a terminal monomer in an overhang of an oligomer, where the UNA monomer is attached to only one monomer at either the propane-1-yl position or the propane-3-yl position. In this form, the UNA monomer does not participate in base pairing. Because the UNA monomers are flexible organic structures, unlike nucleotides, the overhang containing a UNA monomer can be a flexible terminator for the oligomer.

Examples of a UNA monomer as a terminal monomer attached at the propane-3-yl position are shown below.

terminal UNA-A
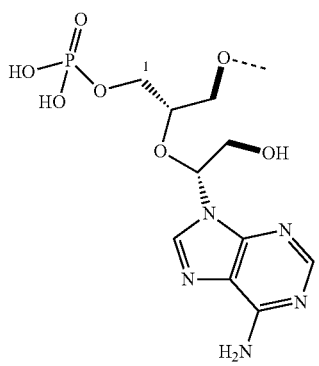

-continued terminal UNA-U
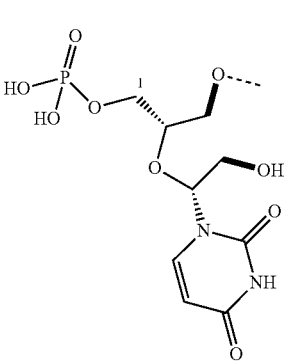

terminal UNA-C
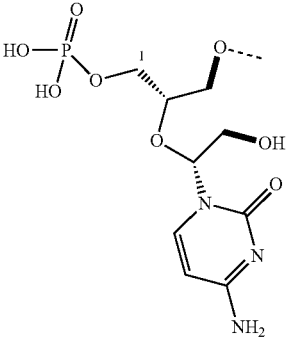

terminal UNA-G
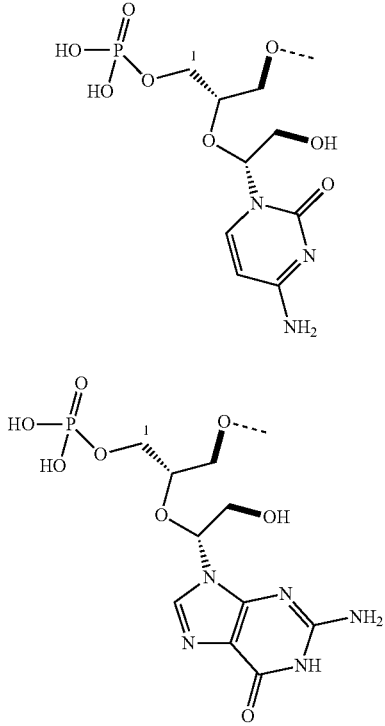

Because a UNA monomer can be a flexible molecule, a UNA monomer as a terminal monomer can assume widely differing conformations. An example of an energy minimized UNA monomer conformation as a terminal monomer attached at the propane-3-yl position is shown below.

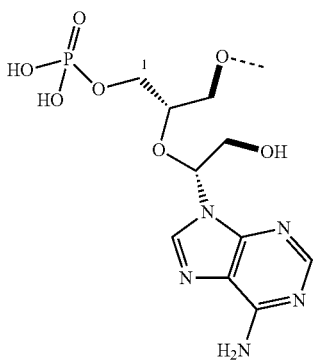

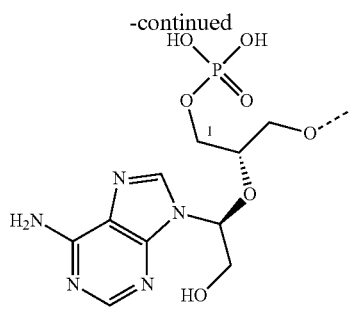

UNA-A terminal forms: the dashed bond shows the propane-3-yl attachment

Thus, UNA oligomers having a terminal UNA monomer are significantly different in structure from conventional nucleic acid agents, such as siRNAs. For example, siRNAs may require that terminal monomers or overhangs in a duplex be stabilized. In contrast, the conformability of a terminal UNA monomer can provide UNA oligomers with different properties.

Among other things, the structure of the UNA monomer allows it to be attached to naturally-occurring nucleotides. A UNA oligomer can be a chain composed of UNA monomers, as well as various nucleotides that may be based on naturally-occurring nucleosides.

In some embodiments, the functional group $R^3$ of a UNA monomer can be —$OR^4$, —$SR^4$, —$NR^4_2$, —$NH(C=O)R^4$, morpholino, morpholin-1-yl, piperazin-1-yl, or 4-alkanoyl-piperazin-1-yl, where $R^4$ is the same or different for each occurrence, and can be H, alkyl, a cholesterol, a lipid molecule, a polyamine, an amino acid, or a polypeptide.

The UNA monomers are organic molecules. UNA monomers are not nucleic acid monomers or nucleotides, nor are they naturally-occurring nucleosides or modified naturally-occurring nucleosides.

A UNA oligomer of this invention is a synthetic chain molecule. A UNA oligomer of this invention is not a nucleic acid, nor an oligonucleotide.

In some embodiments, as shown above, a UNA monomer can be UNA-A (designated Ã), UNA-U (designated Ũ), UNA-C (designated C̃), and UNA-G (designated G̃).

Designations that may be used herein include mA, mG, mC, and mU, which refer to the 2'-O-Methyl modified ribonucleotides.

Designations that may be used herein include lower case c and u, which refer to the 2'-O-methyl modified ribonucleotides.

Designations that may be used herein include dT, which refers to a 2'-deoxy T nucleotide.

Monomers for UNA Oligomers

As used herein, in the context of oligomer sequences, the symbol X represents a UNA monomer.

As used herein, in the context of oligomer sequences, the symbol N represents any natural nucleotide monomer, or a modified nucleotide monomer.

As used herein, in the context of oligomer sequences, the symbol Q represents a non-natural, modified, or chemically-modified nucleotide monomer.

Examples of non-natural, modified, and chemically-modified nucleotide monomers include 2'-O-methyl ribonucleotides, 2'-O-methyl purine nucleotides, 2'-deoxy-2'-fluoro ribonucleotides, 2'-deoxy-2'-fluoro pyrimidine nucleotides, 2'-deoxy ribonucleotides, 2'-deoxy purine nucleotides, universal base nucleotides, 5-C-methyl-nucleotides, and inverted deoxyabasic monomer residues.

Examples of non-natural, modified, and chemically-modified nucleotide monomers include 3'-end stabilized nucleotides, 3'-glyceryl nucleotides, 3'-inverted abasic nucleotides, and 3'-inverted thymidine.

Examples of non-natural, modified, and chemically-modified nucleotide monomers include locked nucleic acid nucleotides, 2'-O,4'-C-methylene-(D-ribofuranosyl) nucleotides, 2'-methoxyethoxy (MOE) nucleotides, 2'-methyl-thioethyl, 2'-deoxy-2'-fluoro nucleotides, and 2'-O-methyl nucleotides.

Examples of non-natural, modified, and chemically-modified nucleotide monomers include 2'-amino nucleotides, 2'-O-amino nucleotides, 2'-C-allyl nucleotides, and 2'-O-allyl nucleotides.

Examples of non-natural, modified, and chemically-modified nucleotide monomers include $N^6$-methyladenosine nucleotides.

Examples of non-natural, modified, and chemically-modified nucleotide monomers include nucleotide monomers with modified bases 5-(3-amino)propyluridine, 5-(2-mercapto)ethyluridine, 5-bromouridine; 8-bromoguanosine, or 7-deazaadenosine.

Examples of non-natural, modified, and chemically-modified nucleotide monomers include 2'-O-aminopropyl substituted nucleotides.

Examples of non-natural, modified, and chemically-modified nucleotide monomers include replacing the 2'-OH group of a nucleotide with a 2'-R, a 2'-OR, a 2'-halogen, a 2'-SR, or a 2'-amino, where R can be H, alkyl, alkenyl, or alkynyl.

Some examples of modified nucleotides are given in Saenger, Principles of Nucleic Acid Structure, Springer-Verlag, 1984.

Details of UNA Oligomer Structure

A UNA oligomer of this invention is a chain molecule. A UNA oligomer can be a duplex pair. Thus, a UNA oligomer can have a first strand of the duplex and a second strand of the duplex, which is complementary to the first strand, although up to three mismatches can occur. A UNA oligomer duplex can have overhangs.

Some UNA oligomers are discussed in U.S. Pat. No. 8,314,227, as well as US Patent Publication No. 20110313020 A1.

The target of a UNA oligomer can be a target nucleic acid. In some embodiments, the target can be any TTR mRNA of a subject. A UNA oligomer can be active for gene silencing in RNA interference.

A UNA oligomer may comprise two strands that together provide a duplex. The duplex may be composed of a first strand, which may also be referred to as a passenger strand or sense strand, and a second strand, which may also be referred to as a guide strand or antisense strand.

In some aspects, a UNA oligomer of this invention can have any number of phosphorothioate intermonomer linkages in any position in any strand, or in both strands of a duplex structure.

In certain embodiments, a UNA oligomer of this invention can have a phosphorothioate intermonomer linkage between the last one or two monomers at either end of any strand.

Examples of UNA oligomers of this invention include duplex pairs, which are in general complementary. Thus, for example, SEQ ID NO:1 can represent a first strand of a duplex and SEQ ID NO:2 can represent a second strand of the duplex, which is complementary to the first strand.

For example, the symbol "N" in the first strand can represent any nucleotide that is complementary to the monomer in the corresponding position in the second strand.

Example UNA oligomers of this disclosure are shown with 2-monomer length overhangs, although overhangs of from 1 to 8 monomers, or longer, can be used.

The symbol "X" in a strand or oligomer represents a UNA monomer.

Further, when the oligomer terminates in a UNA monomer, the terminal position has a 1-end, according to the positional numbering shown above, instead of a 5'-end as for a nucleotide, or the terminal position has a 3-end, according to the positional numbering shown above, instead of a 3'-end as for a nucleotide. For example, the UNA oligomer

```
                                              SEQ ID NO: 1
1-X-N-N-N-N-N-N-N-N-N-N-N-N-N-N-N-N-N-X-X-3
                                              SEQ ID NO: 2
3-X-X-N-N-N-N-N-N-N-N-N-N-X-X-X-X-X-X-N-5'
``` has a UNA monomer 1-end on the first strand, a UNA monomer 3-end on the first strand, a UNA monomer 3-end on the second strand, and a nucleotide 5'-end on the second strand.

In some embodiments, a UNA oligomer of this invention can have one or more UNA monomers at the 1-end of the first strand, and one or more UNA monomers at the 3-end of the first strand.

In further embodiments, a UNA oligomer of this invention can have one or more UNA monomers at the 3-end of the second strand.

In certain embodiments, a duplex UNA oligomer of this invention can have one or more UNA monomers at the 1-end of the first strand, one or more UNA monomers at the 3-end of the first strand, and one or more UNA monomers at the 3-end of the second strand.

A UNA oligomer of this invention the oligomer may have a first strand and a second strand, each of the strands independently being 19-23 monomers in length.

In certain embodiments, a UNA oligomer of this invention may have a first strand that is 19-23 monomers in length.

In certain embodiments, a UNA oligomer of this invention may have a duplex region that is 19-21 monomers in length.

In further embodiments, a UNA oligomer of this invention may have a second strand that is 19-23 monomers in length.

In certain embodiments, a UNA oligomer of this invention may have a first strand that is 19 monomers in length, and a second strand that is 21 monomers in length.

In certain embodiments, a UNA oligomer of this invention may have a first strand that is 20 monomers in length, and a second strand that is 21 monomers in length.

In certain embodiments, a UNA oligomer of this invention may have a first strand that is 21 monomers in length, and a second strand that is 21 monomers in length.

In certain embodiments, a UNA oligomer of this invention may have a first strand that is 22 monomers in length, and a second strand that is 21 monomers in length.

In another aspect, the UNA oligomer may have a blunt end, or may have one or more overhangs. In some embodiments, the first and second strands may be connected with a connecting oligomer in between the strands, and form a duplex region with a connecting loop at one end.

In certain embodiments, an overhang can be one or two monomers in length.

A UNA oligomer can mediate cleavage of a target nucleic acid in a cell. In some processes, the second strand of the UNA oligomer, at least a portion of which can be complementary to the target nucleic acid, can act as a guide strand that can hybridize to the target nucleic acid.

The second strand can be incorporated into an RNA Induced Silencing Complex (RISC). In some embodiments, a UNA oligomer may have a strand that is a DICER substrate.

A UNA oligomer of this disclosure may comprise naturally-occurring nucleic acid nucleotides, and modifications thereof that are compatible with gene silencing activity.

In some aspects, a UNA oligomer is a double stranded construct molecule that is able to inhibit gene expression.

As used herein, the term strand refers to a single, contiguous chain of monomers, the chain having any number of internal monomers and two end monomers, where each end monomer is attached to one internal monomer on one side, and is not attached to a monomer on the other side, so that it ends the chain.

The monomers of a UNA oligomer may be attached via phosphodiester linkages, phosphorothioate linkages, gapped linkages, and other variations.

In some embodiments, a UNA oligomer can include mismatches in complementarity between the first and second strands. In other embodiments, a UNA oligomer may have 1, or 2, or 3 mismatches. The mismatches may occur at any position in the duplex region.

The target of a UNA oligomer can be a target nucleic acid of a target gene.

A UNA oligomer may have one or two overhangs outside the duplex region. The overhangs can be an unpaired portion at the end of the first strand or second strand. The lengths of the overhang portions of the first and second strands can be the same or different.

A UNA oligomer may have at least one blunt end. A blunt end does not have an overhang portion, and the duplex region at a blunt end terminates at the same position for both the first and second strands.

A UNA oligomer can be RISC length, which means that it has a duplex length of less than 25 base pairs.

In certain embodiments, a UNA oligomer can be a single strand that folds upon itself and hybridizes to itself to form a double stranded region having a connecting loop.

Examples of UNA oligomer structures of this invention are shown in Table 1.

TABLE 1

Examples of UNA oligomer structures.

| Oligomer | First strand 1 to 3' | Second strand 5' to 3' |
|---|---|---|
| P15U6 | SEQ ID NO: 3<br>ĞGCCAUGCAUGUGUUCAGAŨ<br>mU | SEQ ID NO: 4<br>UCUGAÃCACAUGCAUGGCCŨ<br>mU |
| P15U7 | SEQ ID NO: 5<br>ĞGCCAUGCAUGUGUUCAGAŨ<br>mU | SEQ ID NO: 6<br>UCUGAAĈACAUGCAUGGCCŨ<br>mU |
| P15U14 | SEQ ID NO: 7<br>ĞGCCAUGCAUGUGUUCAGAŨ<br>mU | SEQ ID NO: 8<br>UCUGAACACAUGCÃUGGCCŨ<br>mU |
| P15U15 | SEQ ID NO: 9<br>ĞGCCAUGCAUGUGUUCAGAŨ<br>mU | SEQ ID NO: 10<br>UCUGAACACAUGCAŨGGCCŨ<br>mU |

TABLE 1-continued

Examples of UNA oligomer structures.

| Oligomer | First strand 1 to 3' | Second strand 5' to 3' |
|---|---|---|
| P15U16 | SEQ ID NO: 11<br>ĞGCCAUGCAUGUGUUCAGAAŨmU | SEQ ID NO: 12<br>UCUGAACACAUGCAUĞGCCŨmU |

Examples of UNA oligomer structures of this invention are shown in Table 2.

TABLE 2

Examples of UNA oligomer structures.

| Oligomer | First strand 1 to 3' | Second strand 5' to 3' |
|---|---|---|
| P16U6 | SEQ ID NO: 13<br>ĞCCAUGCAUGUGUUCAGAAŨmU | SEQ ID NO: 14<br>UUCUGÃACACAUGCAUGGCŨmU |
| P16U7 | SEQ ID NO: 15<br>ĞCCAUGCAUGUGUUCAGAAŨmU | SEQ ID NO: 16<br>UUCUGAÃCACAUGCAUGGCŨmU |

TABLE 2-continued

Examples of UNA oligomer structures.

| Oligomer | First strand 1 to 3' | Second strand 5' to 3' |
|---|---|---|
| P16U15 | SEQ ID NO: 17<br>ĞCCAUGCAUGUGUUCAGAAŨmU | SEQ ID NO: 18<br>UUCUGAACACAUGCÃUGGCŨmU |
| P16U16 | SEQ ID NO: 19<br>ĞCCAUGCAUGUGUUCAGAAŨmU | SEQ ID NO: 20<br>UUCUGAACACAUGCAŨGGCŨmU |
| P16U17 | SEQ ID NO: 21<br>ĞCCAUGCAUGUGUUCAGAAŨmU | SEQ ID NO: 22<br>UUCUGAACACAUGCAUĞGCŨmU |

Examples of sequences of UNA oligomers of this invention targeted to a TTR component are shown in Table 3. "Ref Pos" refers to reference position, which is the numerical position of a reference nucleotide in a TTR mRNA. In Table 3, a UNA oligomer would be composed of pairs SEQ ID NOs:23 and 63, 24 and 64, etc.

TABLE 3

UNA oligomers for TTR component target sequences

| REF POS | SEQ ID NO | Sense (5'-3')<br>SEQ ID NOS: 23 to 62 | SEQ ID NO | Antisense (5'-3')<br>SEQ ID NOS: 63 to 102 |
|---|---|---|---|---|
| 626 | 23 | AUGUAACCAAGAGUAUUCCAUUUUUac | 63 | GUAAAAAUGGAAUACUCUUGGUUACAU |
| 626 | 24 | AUGUAACCAAGAGUAUUCCAUUUUUac | 64 | GUAAAAAUGGAAUACUCUUGGUUACĀŪ |
| 626 | 25 | ĀŪGUAACCAAGAGUAUUCCAUUUUUac | 65 | GUAAAAAUGGAAUACUCUUGGUUACAU |
| 626 | 26 | ĀŪGUAACCAAGAGUAUUCCAUUUUUac | 66 | GUAAAAAUGGAAUACUCUUGGUUACĀŪ |
| 626 | 27 | AUGUAACCAAGAGUAUUCCAUUUUUÂC | 67 | GUAAAAAUGGAAUACUCUUGGUUACĀŪ |
| 626 | 28 | AUGUAACCAAGAGUAUUCCĀŪUUUac | 68 | GUAAAAAUGGAAŪACUCUUGGUUACĀŪ |
| 628 | 29 | GUAACCAAGAGUAUUCCAUUUUUACta | 69 | UAGUAAAAUGGAAUACUCUUGGUUAC |
| 628 | 30 | ĜŪAACCAAGAGUAUUCCAUUUUUACta | 70 | UAGUAAAAUGGAAUACUCUUGGUUAC |
| 628 | 31 | GUAACCAAGAGUAUUCCAUUUUUACta | 71 | UAGUAAAAUGGAAUACUCUUGGUUÂC |
| 628 | 32 | ĜŪAACCAAGAGUAUUCCAUUUUUACta | 72 | UAGUAAAAUGGAAUACUCUUGGUUÂC |
| 628 | 33 | GUAACCAAGAGUAUUCCAUUUUUACŪA | 73 | UAGUAAAAUGGAAUACUCUUGGUUÂC |
| 628 | 34 | GUAACCAAGAGUAUUCCAŪŪUUACUA | 74 | UAGUAAAAUGGĀAUACUCUUGGUUÂC |
| 628 | 35 | ĜUAACCAAGAGUAUUCCAUtt | 75 | AUGGAAUACUCUUGGUUACtt |
| 628 | 36 | GUAACCAAGAGUAUUCCAUtt | 76 | AUGGAAUACUCUUGGUUACŪŪ |
| 628 | 37 | ĜUAACCAAGAGUAUUCCAUtt | 77 | AUGGAAUACUCUUGGUUACŪŪ |
| 628 | 38 | GUAACCAAGAGUAUUCCAŪŪ | 78 | AUGGAAUACUCUUGGUUACŪŪ |
| 628 | 39 | ĜUAACCAAGAGUAUUCCAŪŪ | 79 | AUGGAAUACUCUUGGUUACŪŪ |
| 628 | 40 | GUAACCAAGAGUAUUCCAŪŪ | 80 | AUGGAAŪACUCUUGGUUACŪŪ |
| 628 | 41 | ĜUAACCAAGAGUAUUCCAŪŪ | 81 | AUGGAAŪACUCUUGGUUACŪŪ |
| 628 | 42 | ĜUAACCAAGAGUAUUCCAŪŪ | 82 | AUGGAAŪACUCUUGGUUACĀŪ |
| 628 | 43 | ĜUAACCAAGAGUAUUCCAŪmU | 83 | AUGGAAUACUCUUGGUUACŪmU |

TABLE 3-continued

UNA oligomers for TTR component target sequences

| SEQ REF POS | SEQ ID NO | Sense (5'-3') SEQ ID NOS: 23 to 62 | SEQ ID NO | Antisense (5'-3') SEQ ID NOS: 63 to 102 |
|---|---|---|---|---|
| 628 | 44 | ĞUAACCAAGAGUAUUCCAŪmU | 84 | AUGĞAAUACUCUUGGUUACŪmU |
| 628 | 45 | ĞUAACCAAGAGUAUUCCAŪmU | 85 | AUGGĀAUACUCUUGGUUACŪmU |
| 628 | 46 | ĞUAACCAAGAGUAUUCCAŪmU | 86 | AUGGAĀUACUCUUGGUUACŪmU |
| 626 | 47 | ĀUGUAACCAAGAGUAUUCCŪmU | 87 | GGAAUACUCUUGGUUACAUŪmU |
| 626 | 48 | ĀUGUAACCAAGAGUAUUCCŪmU | 88 | GGAĀUACUCUUGGUUACAUŪmU |
| 626 | 49 | ĀUGUAACCAAGAGUAUUCCŪmU | 89 | GGAAŪACUCUUGGUUACAUŪmU |
| 626 | 50 | ĀUGUAACCAAGAGUAUUCCŪmU | 90 | GGAAUĀCUCUUGGUUACAUŪmU |
| 635 | 51 | ĀGAGUAUUCCAUUUUUACŪmU | 91 | AGUAAAAAUGGAAUACUCŪmU |
| 635 | 52 | ĀGAGUAUUCCAUUUUUACŪmU | 92 | AGUĀAAAAUGGAAUACUCŪmU |
| 635 | 53 | ĀGAGUAUUCCAUUUUUACŪmU | 93 | AGUAĀAAAUGGAAUACUCŪmU |
| 635 | 54 | ĀGAGUAUUCCAUUUUUACŪmU | 94 | AGUAAAĀAUGGAAUACUCŪmU |
| 174 | 55 | ĞACUGGUAUUUGUGUCUGAŪmU | 95 | UCAGACACAAAUACCAGUCĈmA |
| 174 | 56 | ĞACUGGUAUUUGUGUCUGAŪmU | 96 | UCAĞACACAAAUACCAGUCĈmA |
| 174 | 57 | ĞACUGGUAUUUGUGUCUGAŪmU | 97 | UCAGĀCACAAAUACCAGUCĈmA |
| 174 | 58 | ĞACUGGUAUUUGUGUCUGAŪmU | 98 | UCAGAĈACAAAUACCAGUCĈmA |
| 627 | 59 | ŪGUAACCAAGAGUAUUCCAŪmU | 99 | UGGAAUACUCUUGGUUACAŪmU |
| 629 | 60 | ŪAACCAAGAGUAUUCCAUUŪmU | 100 | AAUGGAAUACUCUUGGUUAŪmU |
| 632 | 61 | ĈCAAGAGUAUUCCAUUUUUŪmU | 101 | AAAAAUGGAAUACUCUUGGŪmU |
| 632 | 62 | ĈCAAGAGUAUUCCAUUUUUŪmU | 102 | AAAAAUĞGAAUACUCUUGGŪmU |

In Table 3, lower case designates 2'-deoxyribo-N; upper case designates Ribo-N; underlined-lower case designates 2'-deoxy-N; mA, mG, mC, and mU designate 2'-O-Methyl RNA; and Ā Ū Ğ and Ĉ designate UNA monomers.

In certain embodiments, a UNA oligomer may have a duplex region, and have a UNA monomer in the second strand within the duplex region, where the UNA monomer in the second strand is present in any of positions 1 through 19, counting from the 5' end of the second strand.

In certain embodiments, a UNA oligomer may have a duplex region, and have a UNA monomer in the second strand within the duplex region, where the UNA monomer in the second strand is present in any of positions 6, 7, 14, 15 and 16, counting from the 5' end of the second strand.

In some embodiments, a UNA oligomer may comprise an overhang portion of two monomers in length, or longer, at the 3' end of the first strand, wherein the overhang monomer immediately flanking the duplex portion is a UNA monomer.

In some embodiments, a UNA oligomer may comprise an overhang portion of two monomers in length, or longer, at the 3' end of the second strand, wherein the overhang monomer immediately flanking the duplex portion is a UNA monomer.

Methods for Treating Amyloidosis

Methods of this invention include the treatment and prevention of TTR-related amyloidosis in human and mammalian subjects.

In the methods of this invention, a subject in need of treatment or prevention can be administered an effective amount of a UNA oligomer. Administration can be performed for 1, 2, or up to 7 days, or 1, 2, 3, or up to 4 weeks, or longer.

The subject may have TTR-related amyloidosis, also known as ATTR.

In particular, a subject can have a V30M gene. The methods of this invention can selectively reduce V30M TTR in the subject.

In some embodiments, a method of this invention can selectively reduce V30M TTR in the subject by at least 10%, as compared to control. In certain embodiments, V30M TTR in the subject can be reduced by at least 20%, or 30%, or 50%, as compared to control.

An effective amount of a UNA oligomer of this invention can be a dose ranging from 0.001 mg/kg to 50.0 mg/kg, or from 0.001 mg/kg to 10.0 mg/kg.

In the methods of this invention, TTR mRNA expression can be reduced in a subject for at least 5 days. In certain embodiments, TTR mRNA expression can be reduced in a subject for at least 10 days, or 15 days.

In the methods of this invention, peripheral neuropathy or autonomic neuropathy in the subject can be reduced.

In the methods of this invention, peripheral neuropathy or autonomic neuropathy in the subject can be reduced. In some embodiments, a subject may undergo reduced lower extremity weakness, reduced pain, or improved sensation. Methods of this invention can reduce occurrence of vitreous opacities in the subject.

In the methods of this disclosure, the administration of a UNA oligomer may not result in an inflammatory response.

In further embodiments, this invention includes methods for inhibiting expression of a TTR gene in a cell, by treating the cell with a UNA oligomer.

In additional embodiments, this invention includes methods for inhibiting expression of a TTR gene in a mammal, by administering to the mammal a composition containing a UNA oligomer.

Pharmaceutical Compositions

In some aspects, this invention provides pharmaceutical compositions containing a UNA oligomer and a pharmaceutically acceptable carrier.

In further aspects, this invention includes nanoparticle compositions that can encapsulate and deliver a UNA oligomer to cells with surprisingly advantageous potency. The nanoparticles can be formed with lipid molecules, for example, any one or more of the compounds ATX-001 to ATX-032 disclosed in WO/2015/074085. In certain embodiments, lipid nanoparticles of this invention can be formed with compound ATX-002, as disclosed in WO/2015/074085, and the nanoparticles can encapsulate the UNA oligomer.

A pharmaceutical composition can be capable of local or systemic administration. In some aspects, a pharmaceutical composition can be capable of any modality of administration. In certain aspects, the administration can be intravenous, subcutaneous, pulmonary, intramuscular, intraperitoneal, dermal, oral, or nasal administration.

Embodiments of this invention include pharmaceutical compositions containing a UNA oligomer in a lipid formulation.

In some embodiments, a pharmaceutical composition may comprise one or more lipids selected from cationic lipids, anionic lipids, sterols, pegylated lipids, and any combination of the foregoing.

In certain embodiments, a pharmaceutical composition can be substantially free of liposomes.

In further embodiments, a pharmaceutical composition can include liposomes.

In additional embodiments, a pharmaceutical composition can contain a UNA oligomer within a viral or bacterial vector.

A pharmaceutical composition of this disclosure may include carriers, diluents or excipients as are known in the art. Examples of pharmaceutical compositions are described, for example, in *Remington's Pharmaceutical Sciences*, Mack Publishing Co. (A. R. Gennaro ed. 1985).

Examples of excipients for a pharmaceutical composition include antioxidants, suspending agents, dispersing agents, preservatives, buffering agents, tonicity agents, and surfactants.

EXAMPLES

Example 1

FIG. 1 shows the single nucleotide polymorph (SNP) that exists at position 284 in the V30M mutation of the human TTR mRNA, as compared to the wild type (WT) TTR mRNA. Conventional siRNAs that are complementary to the WT mRNA were tiled around position 284. FIG. 2 shows that the conventional siRNAs complementary to the WT mRNA have limited activity in silencing the WT TTR gene, as measured by TTR knockdown in HepG2 cells. Positions 5, 9, 14 and 15 appear to be more accessible to silencing than other positions. FIG. 3 shows conventional siRNAs that were complementary to the V30M mRNA were tiled around position 284. Four conventional siRNA variations, namely V30M-P5, V30M-P9, V30M-P14, and V30M-P15, were prepared. Also, as shown in FIG. 3, two gene reporter variants, V30V and V30M, each bearing nucleotide sequence 264 to 304 of human TTR, V30V being without the point mutation at position 284, and V30M containing the point mutation at position 284, were prepared and used in the PSICHECK reporter system in the 3'-UTR region of Luciferase gene.

Example 2

Figure 4:
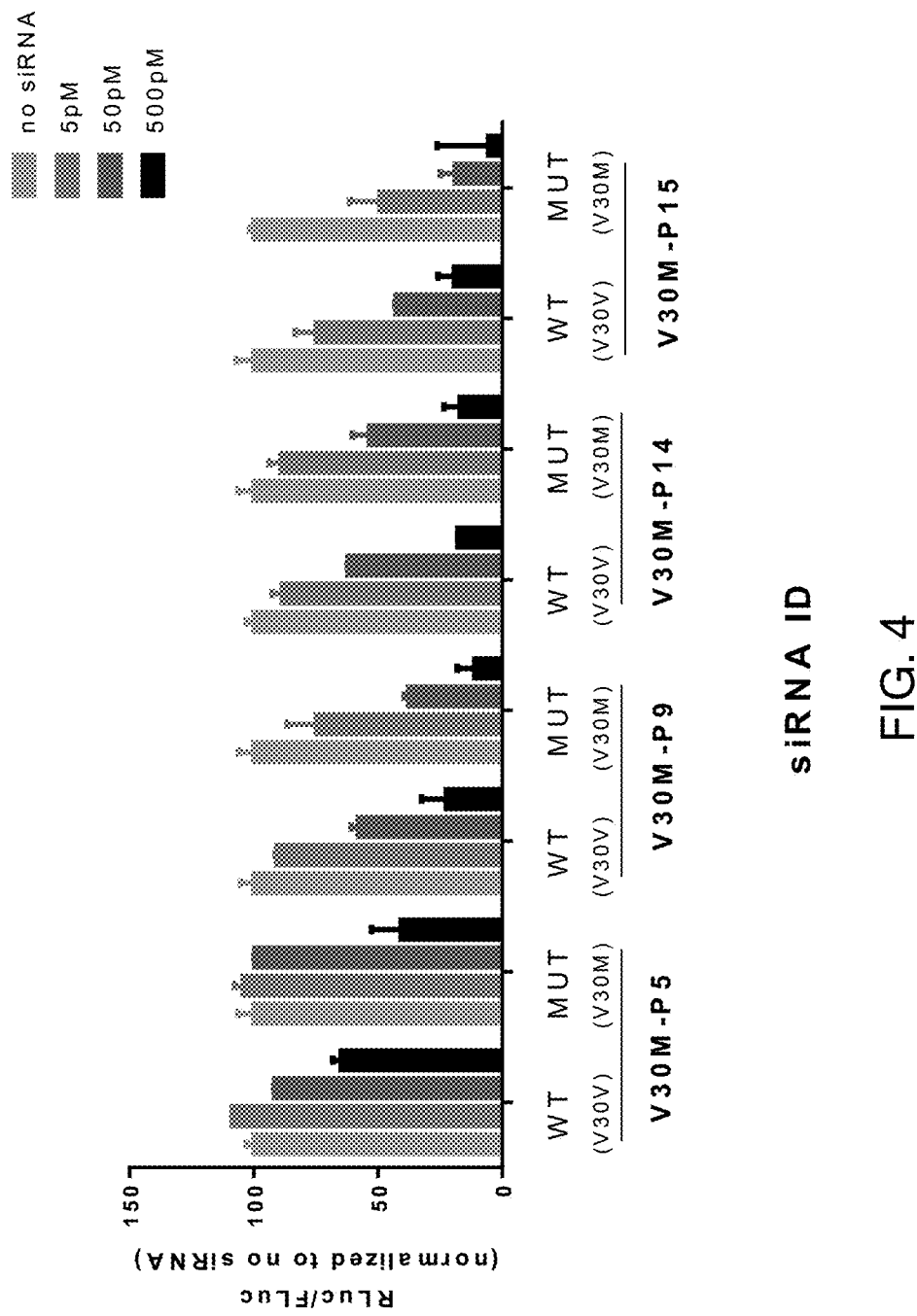
FIG. 4 shows the activity of the four conventional siRNA variations V30M-P5, V30M-P9, V30M-P14, and V30M-P15 measured in the PSICHECK reporter assay against V30V and V30M gene reporter variants. The conventional siRNA variations V30M-P5, V30M-P9, and V30M-P15 were more effective against V30M than V30V. The conventional siRNA variation V30M-P14 was not more effective against V30M than V30V.
Figure 5:
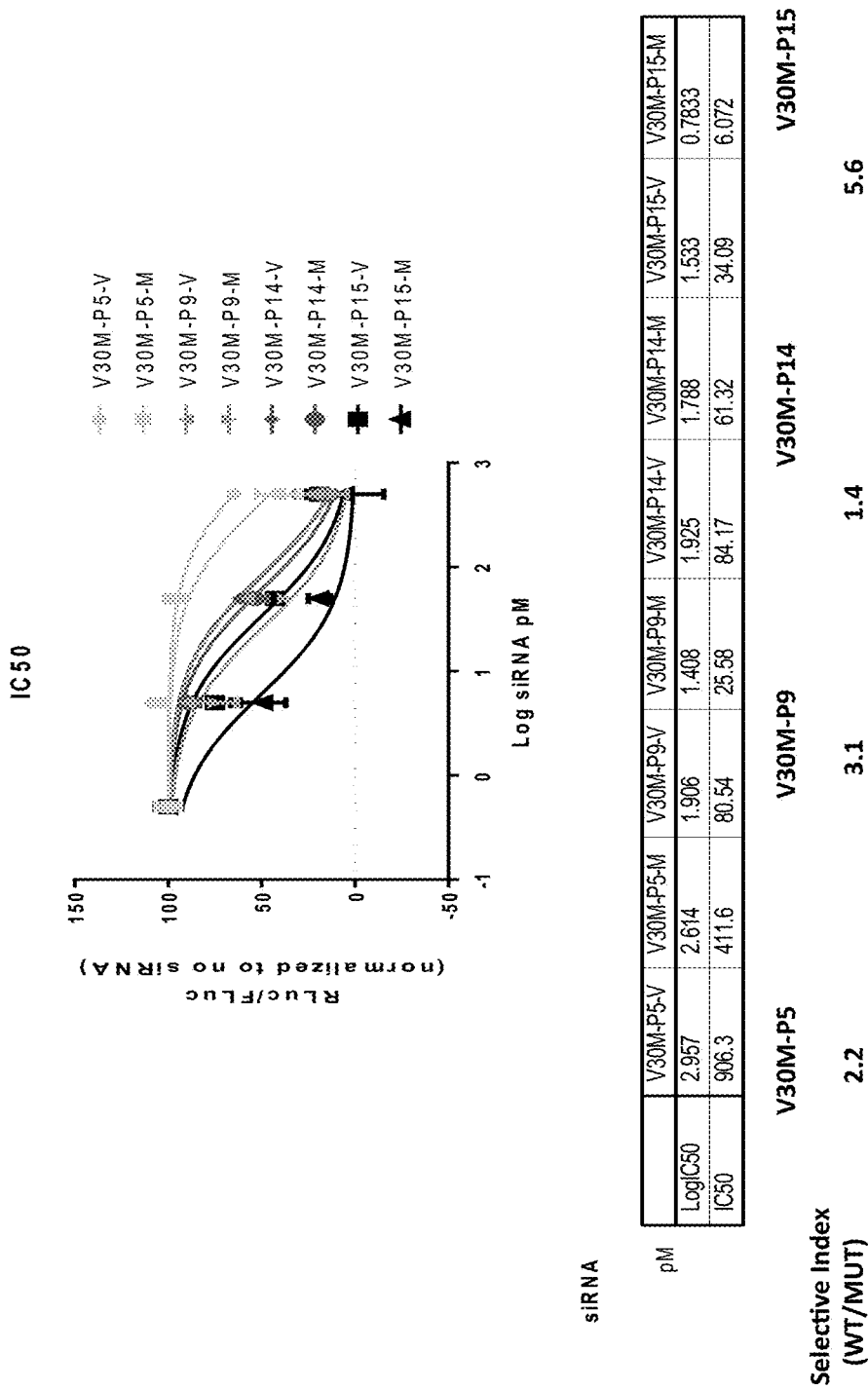
FIG. 5 shows IC50 analysis for the four conventional siRNA variations V30M-P5, V30M-P9, V30M-P14, and V30M-P15 measured in the PSICHECK reporter assay against V30V and V30M gene reporter variants. The conventional V30M-P15 variant was 5.6 times more effective against V30M than V30V. Thus, the selectivity of the conventional siRNAs against V30M over V30V was no more than 5.6.

FIG. 4 shows the activity of the four conventional siRNA variations V30M-P5, V30M-P9, V30M-P14, and V30M-P15 as measured in the PSICHECK reporter assay against V30V and V30M gene reporter variants. The conventional siRNA variations V30M-P5, V30M-P9, and V30M-P15 were more effective against V30M than V30V. The conventional siRNA variation V30M-P14 was not more effective against V30M than V30V. FIG. 5 shows IC50 analysis for the four conventional siRNA variations V30M-P5, V30M-P9, V30M-P14, and V30M-P15 measured in the PSICHECK reporter assay against V30V and V30M gene reporter variants. The conventional V30M-P15 variant was 5.6 times more effective against V30M than V30V. Thus, the selectivity of the conventional siRNAs against V30M over V30V was no more than 5.6.

Example 3

FIG. 6 shows the structure of UNA oligomers that were effective in silencing V30M TTR, as measured in the PSICHECK reporter assay. Each of the UNA oligomer embodiments, P15U6, P15U7, P15U14, P15U15, and P15U16, contained four UNA monomers. In each UNA oligomer, a first UNA monomer was located at the 5' end of the first strand, also called the passenger strand. In each UNA oligomer, the second strand, also called the guide strand, formed a duplex region of 19 monomers length with the first strand. Each UNA oligomer had a duplex region of 19 monomers, and a two-monomer overhang at each end. In each UNA oligomer, a second UNA monomer was located at the 3' end of the first strand, in the $20^{th}$ position, which is in an overhang portion. In each UNA oligomer, a third UNA monomer was located at the 3' end of the second strand, in the $20^{th}$ position, which is in an overhang portion. In the UNA oligomer embodiments, P15U6, P15U7, P15U14, P15U15, and P15U16, a fourth UNA monomer was located in the second strand at positions 6, 7, 14, 15 and 16, respectively, counting from the 5' end of the second strand.

Example 4

Figure 7:
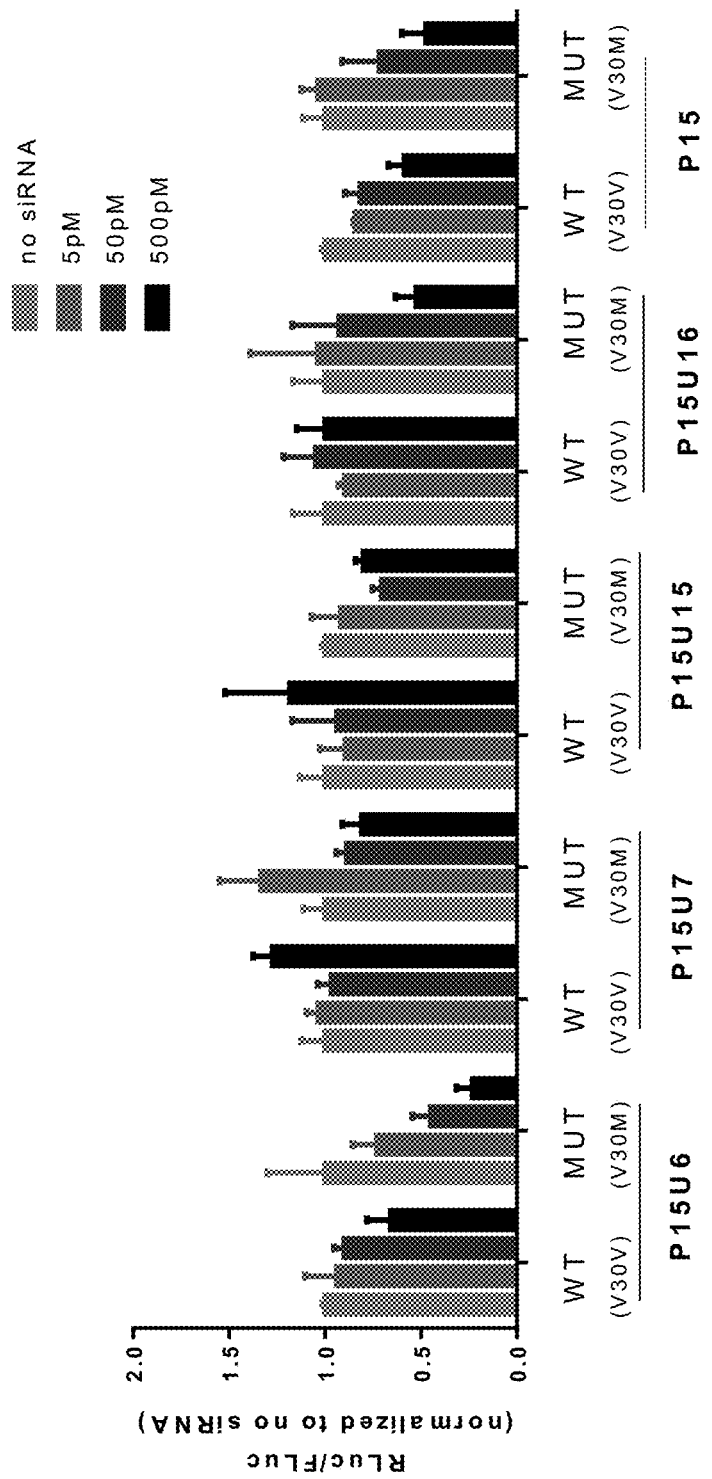
FIG. 7 shows the activity of UNA oligomers P15U6, P15U7, P15U15, and P15U16, measured in the PSICHECK reporter assay against V30V and V30M gene reporter variants, as compared to the conventional siRNA V30M-P15. For each of the UNA oligomer embodiments, P15U6, P15U7, P15U15, and P15U16, the UNA oligomers were more effective against V30M than V30V. Surprisingly, the activity of the UNA oligomer P15U6 was substantially and advantageously superior to the activity of the conventional siRNA V30M-P15, where each is targeted to V30M. Furthermore.

FIG. 7 shows the activity of UNA oligomers P15U6, P15U7, P15U15, and P15U16, measured in the PSICHECK reporter assay against V30V and V30M gene reporter variants, as compared to the conventional siRNA V30M-P15. For each of the UNA oligomer embodiments, P15U6, P15U7, P15U15, and P15U16, the UNA oligomers were more effective against V30M than V30V. Surprisingly, the activity of the UNA oligomer P15U6 was substantially and advantageously superior to the activity of the conventional siRNA V30M-P15, where each is targeted to V30M. Furthermore, FIG. 7 shows the surprising and unexpected result that the selectivity of the UNA oligomers, P15U6, P15U7, P15U15, and P15U16, against V30M over V30V was substantially greater than for the conventional siRNA V30M-P15. In particular, the selectivity of UNA oligomer P15U6 against V30M over V30V was 24, meaning that the IC50 of UNA oligomer P15U6 against V30M (37.6 pM) was 24 times lower than the IC50 of UNA oligomer P15U6 against V30V (919.9 pM). This selectivity was advantageously 4-fold superior to the selectivity of 5.6 shown by the conventional siRNA.

Example 5

FIG. 8 shows the structure of UNA oligomers that were effective in silencing V30M TTR, as measured in the PSI-CHECK reporter assay. Each of the UNA oligomer embodiments, P16U6, P16U7, P16U15, P16U16, and P16U17, contained four UNA monomers. In each UNA oligomer, a first UNA monomer was located at the 5' end of the first strand, also called the passenger strand. In each UNA oligomer, the second strand, also called the guide strand, formed a duplex region of 19 monomers length with the first strand. Each UNA oligomer had a duplex region of 19 monomers, and a two-monomer overhang at each end. In each UNA oligomer, a second UNA monomer was located at the 3' end of the first strand, in the 20$^{th}$ position, which is in an overhang portion. In each UNA oligomer, a third UNA monomer was located at the 3' end of the second strand, in the 20$^{th}$ position, which is in an overhang portion. In the UNA oligomer embodiments, P16U6, P16U7, P16U15, P16U16, and P16U17, a fourth UNA monomer was located in the second strand at positions 6, 7, 15, 16 and 17, respectively, counting from the 5' end of the second strand.

Example 6

Figure 9:
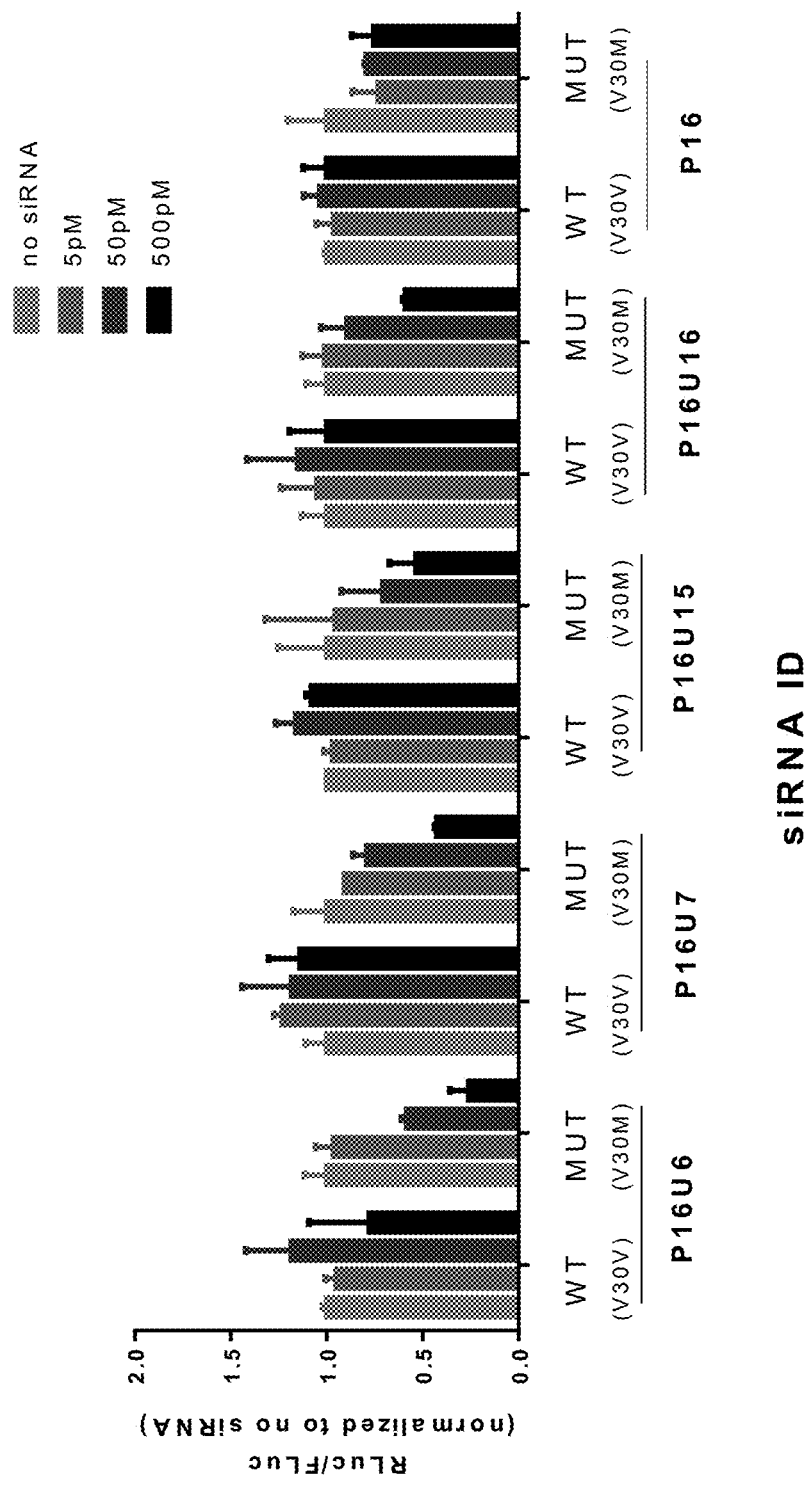
FIG. 9 shows the activity of UNA oligomers P16U6, P16U7, P16U15, and P16U16, measured in the PSICHECK reporter assay against V30V and V30M gene reporter variants, as compared to the conventional siRNA V30M-P16. For each of the UNA oligomer embodiments, P16U6, P16U7, P16U15, and P16U16, the UNA oligomers were more effective against V30M than V30V. Surprisingly, the activity of each of the UNA oligomers P16U6, P16U7, P16U15, and P16U16, was substantially and advantageously superior to the activity of the conventional siRNA V30M-P16, where each is targeted to V30M. Furthermore.

FIG. 9 shows the activity of UNA oligomers P16U6, P16U7, P16U15, and P16U16, measured in the PSICHECK reporter assay against V30V and V30M gene reporter variants, as compared to the conventional siRNA V30M-P16. For each of the UNA oligomer embodiments, P16U6, P16U7, P16U15, and P16U16, the UNA oligomers were more effective against V30M than V30V. Surprisingly, the activity of each of the UNA oligomers P16U6, P16U7, P16U15, and P16U16, was substantially and advantageously superior to the activity of the conventional siRNA V30M-P16, where each is targeted to V30M. Furthermore, FIG. 9 shows the surprising and unexpected result that the selectivity of the UNA oligomers, P16U6, P16U7, P16U15, and P16U16, against V30M over V30V was substantially greater than for the conventional siRNA V30M-P16. In particular, the selectivity of UNA oligomer P16U6 against V30M over V30V was 23, meaning that the IC50 of UNA oligomer P16U6 against V30M (92.4 pM) was 23 times lower than the IC50 of UNA oligomer P16U6 against V30V (2119 pM). This selectivity was advantageously 4-fold superior to the selectivity of 5.6 shown by the conventional siRNA.

Figure 10:
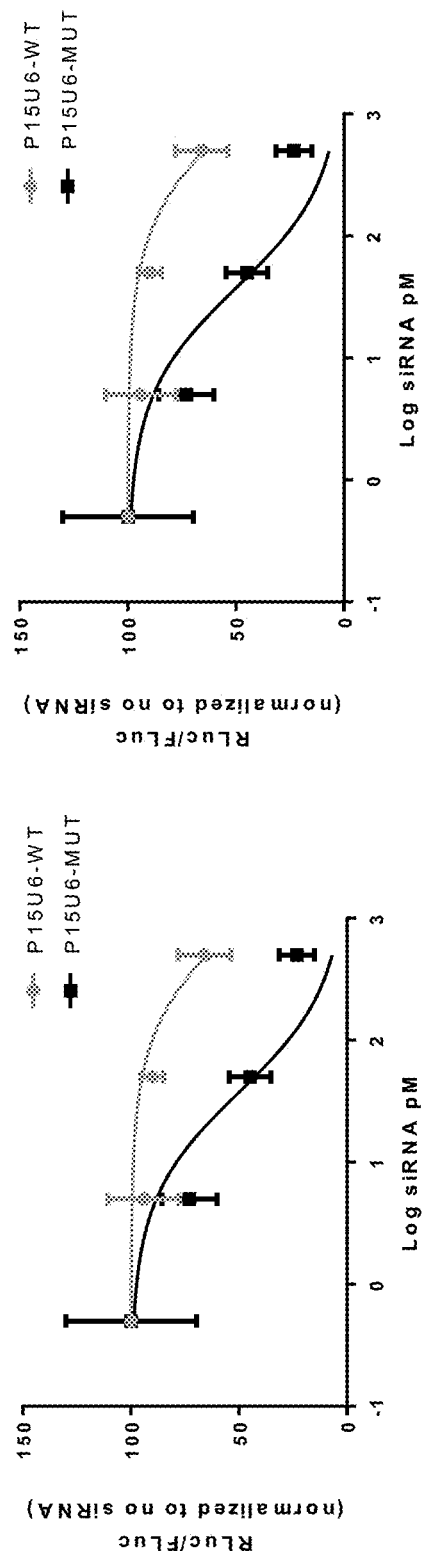
FIG. 10 (left) shows the selectivity of UNA oligomer P15U6 against V30M over V30V. The IC50 of UNA oligomer P15U6 against V30M (37.6 pM) was 24 times lower than the IC50 of UNA oligomer P15U6 against V30V (919.9 pM). This selectivity was advantageously 4-fold superior to the selectivity of 5.6 shown in FIG. 5 above for the conventional siRNA.

FIG. 10 (left) shows the selectivity of UNA oligomer P15U6 against V30M over V30V. The IC50 of UNA oligomer P15U6 against V30M (37.6 pM) was 24 times lower than the IC50 of UNA oligomer P15U6 against V30V (919.9 pM). This selectivity was advantageously 4-fold superior to the selectivity of 5.6 shown by the conventional siRNA. FIG. 10 (right) shows the surprising and unexpected result that the IC50 of UNA oligomer P16U6 against V30M (92.4 pM) was 23 times lower than the IC50 of UNA oligomer P16U6 against V30V (2119 pM). This selectivity was advantageously 4-fold superior to the selectivity of 5.6 shown by the conventional siRNA.

Example 7: UNA Oligomers Reduce V30M TTR Deposits In Vivo

Transgenic mice for human TTR V30M overexpression are used at 6 months age. TTR wild-type and TTR knockout mice are used as controls. Animals are housed in controlled environment, and euthanized with ketamine and medetomidine.

For TTR gene silencing, the TTR UNA oligomer, as well as controls, are delivered in liposome formulations. Mice are injected in the tail vein with TTR UNA oligomer (n=6), at a concentration of 1 mg/kg. Untreated age-matched controls are treated with blank formulation. One injection is given per week for 4 weeks, and animals are sacrificed 48 h after last injection. Liver and colon are removed and collected to 10% formalin and frozen.

Liver and colon mRNA are isolated using phenol extraction (Invitrogen). Sciatic nerve from V30M mice is dissected from other tissue, and mRNA is extracted with a RNeasy Mini column (Qiagen). cDNA is synthesized with a SuperScript double-stranded cDNA Kit (Invitrogen). Extracted RNA is validated with Experion RNA StdSens Analysis Kit (Bio-Rad). qPCR is performed with primers and iQ Syber Green Super Mix (Bio-Rad). Double immunofluorescence analysis is performed with sciatic nerve, dorsal root ganglia, and colon from V30M animals that is removed and treated as above. Comparisons are performed with Student T-test or One-way ANOVA. Data are expressed as mean values±standard error (SEM). p-values less than 0.05 are considered significant.

Injection of a composition containing one or more UNA oligomers in V30M mice reduces the V30M TTR deposits in sciatic nerve, dorsal root ganglia, and colon by at least 90% over controls.

Injection of a composition containing any one of UNA oligomers P15U6, P15U7, P15U15, or P15U16, or any combination of these UNA oligomers, in V30M mice reduces the V30M TTR deposits in sciatic nerve, dorsal root ganglia, and colon by at least 90% over controls.

Example 8: UNA Oligomers Reduce TTR Protein In Vivo Primate

A single-dose, pharmacokinetic and pharmacodynamic study of liposomally formulated UNA Oligomers targeting transthyretin (TTR) mRNA following intravenous infusion in Cynomolgus monkeys was performed.

Cynomolgus monkeys (*Macaca fascicularis*) were selected for this study because the TTR mRNA of Cynomolgus monkeys is homologous to human TTR mRNA, making them a good model for screening the potency of UNA oligomers targeting to TTR mRNA.

In this study, the knockdown of Transthyretin protein was evaluated as a result of treatment with UNA oligomers targeting Transthyretin TTR mRNA, based on SEQ ID NOs:46/86, 59/99, and 60/100, delivered in a liposomal formulation to male Cynomolgus monkeys. Measurements were made following a single intravenous (IV) dose administration. TTR protein concentration in plasma samples was assessed by LC-MS/MS at various time points.

Twenty-four (24) Cynomolgus non-naïve and naïve monkeys were used in this study. There were eight (8) groups of animals in the study with three (3) per group and three (3) extra animals. The animals weighed 2.4 to 6.8 kg and were 3 to 6 years old at pre-study physical examination. Animals were housed in a temperature- and humidity-monitored environment. The targeted range of temperature and relative humidity was from 18° C. to 29° C., and from 35% to 70%, respectively. An automatic lighting system provided a 12-hour light/dark cycle. Previously quarantined animals were acclimated to the study room for a minimum of 14 days prior to initiation of dosing. Acclimation phase data was collected from all animals.

Animals in Groups 1 through 8 were administered the test articles on Day 1 at 0.3 mg/kg, dose volume 6.25 mL/kg, concentration 0.048 mg/mL. Doses were administered as a 15-minute intravenous (IV) infusion, ±1 minute, using a pump and disposable syringe.

For each animal, infusion start and end times were recorded; and subsequent sample collection target times were determined based on infusion end time (t=0). All blood specimens, approximately 1 mL, were collected by venipuncture from a peripheral vein from restrained, conscious animals.

Knockdown of TTR was observed in all treated groups with observation at Days 10 and 20 after dosing. The study period was lengthened to 50 days for one group to observe long-term effects.

Figure 11:
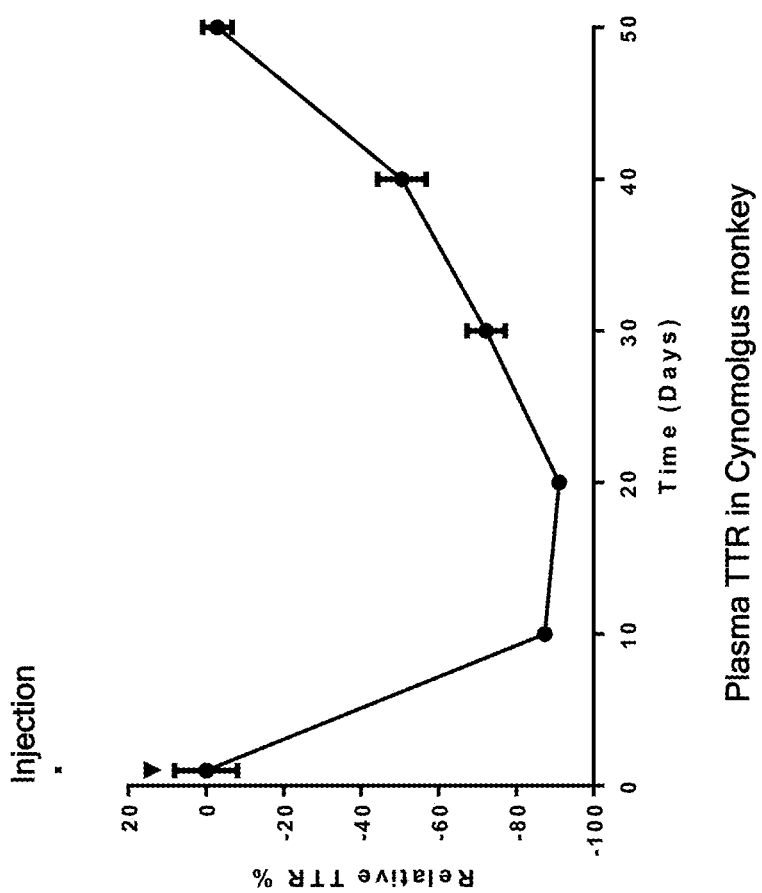
FIG. 11 shows knockdown of Transthyretin protein in vivo as a result of treatment with UNA oligomers targeting Transthyretin TTR mRNA, delivered in a liposomal formulation to male Cynomolgus monkeys. Measurements were made following a single intravenous (IV) dose administration. TTR protein concentration in plasma samples was assessed by LC-MS/MS at various time points. Animals were administered test doses on Day 1 at 0.3 mg/kg. Doses were administered as a 15-minute intravenous (IV) infusion, ±1 minute, using a pump and disposable syringe.

Referring to FIG. 11, knockdown of Transthyretin protein in vivo was achieved as a result of treatment with UNA oligomers targeting Transthyretin TTR mRNA, delivered in a liposomal formulation to male Cynomolgus monkeys. Measurements were made following a single intravenous (IV) dose administration. TTR protein concentration in plasma samples was assessed by LC-MS/MS at various time points.

As shown in FIG. 11, a single injection in the primates of a UNA oligomer targeted to TTR surprisingly knocked down TTR protein levels to below 50% with a continuous duration of more than one month (30 days).

FIG. 11 shows the unexpectedly advantageous result of over 91% knockdown of TTR in the primates at 20 days, and more than 70% knockdown with a continuous duration of more than 20 days.

The Monkey TTR SRM assay was used, which is a high throughput absolute protein quantitation assay using Selected Reaction Monitoring (SRM) technology platform. In a single SRM assay, the panel can multiplex up to 200 proteins. The assay was performed on a targeted absolute protein quantitation platform, where the key technology was SRM, sometimes also referred to as Multiple Reaction Monitoring (MRM). In a triple-quadrupole (QQQ) mass spectrometer, SRM/MRM is a tandem selection process where selecting peptides by precursor m/z is followed by selecting fragmentations (transitions) of the targeted peptide. Further, coupled with liquid chromatography and the addition of heavy labeled internal standards, SRM/MRM is a highly selective, sensitive technology to quantify designated protein with precision.

All publications, patents and literature specifically mentioned herein are incorporated by reference for all purposes.

It is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be encompassed by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprises," "comprising", "containing," "including", and "having" can be used interchangeably.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

What is claimed is:

1. A pharmaceutical composition comprising a UNA oligomer targeted to TTR and a pharmaceutically acceptable carrier, wherein
the UNA oligomer comprises a first strand and a second strand, each of the strands being 19-29 monomers in length, the monomers comprising UNA monomers and nucleic acid monomers, wherein the oligomer has a duplex structure of from 14 to 29 monomers in length; and
a contiguous portion of the second strand has a sequence according to the entire sequence of one of SEQ ID NOs:63-102.

2. The pharmaceutical composition of claim 1, wherein the carrier is a lipid formulation.

3. The pharmaceutical composition of claim 1, wherein the carrier is a lipid formulation comprising liposomes that encapsulate the UNA oligomer.

4. The pharmaceutical composition of claim 1, wherein the carrier is a lipid formulation comprising any one or more of the compounds ATX-001 to ATX-032.

5. The pharmaceutical composition of claim 1, wherein the carrier includes one or more lipids selected from cationic lipids, anionic lipids, sterols, pegylated lipids, and any combination of the foregoing.

6. The pharmaceutical composition of claim 1, wherein upon administering a single intravenous dose to a primate, the pharmaceutical composition reduces TTR protein in the primate by at least 90% after 20 days.

7. The pharmaceutical composition of claim 1, wherein upon administering a single intravenous dose to a primate, the pharmaceutical composition reduces TTR protein in the primate by at least 70% for a period of at least 20 days.

8. The pharmaceutical composition of claim 1, wherein upon administering a single intravenous dose to a primate, the pharmaceutical composition reduces TTR protein in the primate by at least 50% for a period of at least 30 days.

9. A method for treating or preventing TTR-related amyloidosis in a primate in need, the method comprising administering to the primate an effective amount of a pharmaceutical composition comprising a UNA oligomer targeted to TTR and a pharmaceutically acceptable carrier, wherein
the UNA oligomer comprises a first strand and a second strand, each of the strands being 19-29 monomers in length, the monomers comprising UNA monomers and nucleic acid monomers, wherein the oligomer has a duplex structure of from 14 to 29 monomers in length; and
a contiguous portion of the second strand has a sequence according to the entire sequence of one of SEQ ID Nos:63-102.

10. The method of claim 9, wherein the TTR-related amyloidosis is ATTR.

11. The method of claim 9, wherein the primate is human.

12. The method of claim 9, wherein the administering is intravenous, subcutaneous, pulmonary, intramuscular, intraperitoneal, or dermal.

13. The method of claim 9, wherein the effective amount is a dose of from 0.001 to 10.0 mg/kg.

14. The method of claim 9, wherein upon administering a single dose to the primate, the pharmaceutical composition reduces TTR protein in the primate by at least 70% after 20 days.

15. The method of claim 9, wherein upon administering a single dose to the primate, the pharmaceutical composition reduces TTR protein in the primate by at least 90% after 20 days.

16. The method of claim 9, wherein upon administering a single dose to the primate, the pharmaceutical composition reduces TTR protein in the primate by at least 70% for a period of at least 10 days.

17. The method of claim 9, wherein upon administering a single dose to the primate, the pharmaceutical composition reduces TTR protein in the primate by at least 70% for a period of at least 20 days.

18. The method of claim 9, wherein upon administering a single dose to the primate, the pharmaceutical composition reduces TTR protein in the primate by at least 50% for a period of at least 30 days.

* * * * *

UNITED STATES PATENT AND TRADEMARK OFFICE
CERTIFICATE OF CORRECTION

PATENT NO. : 10,604,758 B2
APPLICATION NO. : 15/859571
DATED : March 31, 2020
INVENTOR(S) : Tachikawa et al.

Page 1 of 1

It is certified that error appears in the above-identified patent and that said Letters Patent is hereby corrected as shown below:

On the Title Page

On Page 2, in Item (63), under "Related U.S. Application Data", in Column 1, Line 1, delete "continuation" and insert -- continuation in part --, therefor.

On Page 3, in Item (56), under "OTHER PUBLICATIONS", in Column 2, Line 10, delete "4'-C-(Hydroxymethyl" and insert -- 4'-C-(Hydroxymethyl) --, therefor.

In the Specification

In Column 6, Line 35, delete "100551 Homo" and insert -- Homo --, therefor.

In Column 11, Line 43, delete "G)." and insert -- Ğ). --, therefor.

In Column 12, Line 7, delete "2'-0,4'-C-methylene-(D-ribofuranosyl)" and insert -- 2'-O,4'-C-methylene-(D-ribofuranosyl) --, therefor.

Signed and Sealed this
Third Day of November, 2020

Andrei Iancu
*Director of the United States Patent and Trademark Office*